(12) United States Patent
Heldin et al.

(10) Patent No.: US 6,939,849 B1
(45) Date of Patent: Sep. 6, 2005

(54) RECOMBINANT PDGF A-CHAIN HOMODIMERS AND METHODS OF USE

(75) Inventors: Carl-Henrik Heldin, Uppsala (SE); Christer Betsholtz, Uppsala (SE); Bengt Westermark, Uppsala (SE); Timothy J. Knott, London (GB); James Scott, Harrow (GB); Graeme I. Bell, San Francisco, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 08/453,350

(22) Filed: May 30, 1995

Related U.S. Application Data

(63) Continuation of application No. 08/260,203, filed on Jun. 8, 1994, which is a continuation of application No. 07/942,379, filed on Sep. 9, 1992, which is a continuation of application No. 07/633,671, filed on Dec. 26, 1990, which is a division of application No. 07/574,540, filed on Aug. 27, 1990, now Pat. No. 5,219,759, which is a continuation of application No. 07/041,299, filed on Apr. 22, 1987.

(51) Int. Cl.$^7$ .................. A61K 38/18; C07K 14/49; C12N 15/18; C12N 15/63; C12N 1/21
(52) U.S. Cl. ................ 514/12; 514/2; 530/399; 435/69.1; 435/320.1; 435/325
(58) Field of Search ............ 514/2, 12, 8; 530/399, 530/350, 324, 380; 435/69.1, 320.1, 325, 252.3

(56) References Cited

U.S. PATENT DOCUMENTS

| | | | |
|---|---|---|---|
| 4,766,073 A | 8/1988 | Murray et al. | 435/172.3 |
| 4,769,328 A | 9/1988 | Murray et al. | 435/68 |
| 4,801,542 A | 1/1989 | Murray et al. | 435/172.3 |
| 4,845,075 A | 7/1989 | Murray et al. | 514/12 |
| 4,849,407 A | 7/1989 | Murray et al. | 514/12 |
| 4,889,919 A | 12/1989 | Murray et al. | 530/357 |
| 5,045,633 A | 9/1991 | Murray et al. | |
| 5,128,321 A | 7/1992 | Murray et al. | |
| 5,498,600 A | 3/1996 | Murray | 514/12 |
| 6,004,929 A * | 12/1999 | Murray et al. | |

FOREIGN PATENT DOCUMENTS

| | | |
|---|---|---|
| EP | 0177957 | 4/1986 |
| EP | 0 259 632 | 3/1988 |

OTHER PUBLICATIONS

Johnnson et al. *Biochem. Biophys Res Comm.* 104(1) p. 66–74 (1982).*
Antoniades et al *Science* 220: p. 963–965 (1983).*
Tong B. D., et al., "Cloning of the A–Chain of PDGF and A–Chain Expression in Human Endothelial Cells" (Abstract No. A 175) *J. of Cellular Biochemistry* (1987) p. 44.
Hoppe et al., *FEBS Letters* (1987) 223 (2) :243–246.
Collins et al., *Nature* (1985) 316:748–750.
Johnsson et al., *EMBO J.* (1984) 3(5) :921–928.
Waterfield et al., *Nature* (1983) 304:35–39.
Heldin et al., *Nature* (1986) 319:511–514.
Betsholtz et al., *Nature* (1986) 320:695–699.
Westermark et al., *Proc. Natl. Acad. Sci. USA* (1986) 83:7197–7200.
Doolittle et al., *Science* (1983) 221:275–277.
Gazit et al., *Cell* (1984) 39:89–97.
Clarke et al., *Nature* (1984) 308:464–467.
Kelly et al., *EMBO J.* (1985) 4: (13A) :3399–3405.
Devare et al., *Cell* (1984) 36:43–49.
Wang et al., *J. Biol. Chem.* (1984) 259(17) :10645–10648.
Hannink et al., *Molecular and Cellular Biol.* (1986) 6(4) : 1343–1348.
Fry et al., *J. Cellular Physiol.* (1986) 128:313–321.
Robbins et al., *Nature* (1983) 305:605–608.
King et al., *Proc. Natl. Acad. Sci. USA* (1985) 82:5295–5299.

* cited by examiner

*Primary Examiner*—Christine J. Saoud
(74) *Attorney, Agent, or Firm*—Roberta L. Robins; Lisa E. Alexander; Robert P. Blackburn

(57) ABSTRACT

DNA encoding two forms of PDGF A-chain polypeptide, the construction of expression vectors for expressing such DNA in yeast and mammalian cells, and the expression of such DNA in yeast and mammalian cells to produce active PDGF A-chain homodimer and active PDGF A-chain/B-chain heterodimer are disclosed.

12 Claims, 14 Drawing Sheets

Sequence of the Human Platelet-Derived Growth Factor A-Chain Clone Uppsala-D1

GAATTCCGTCCGCAATATGCAGAATTACCGGCCGGGTCGTCGTCCTCTGAAGCAGCAGCGCGGGGAGCAGCGCGGCGGCCCAGCACCGGAACGCACCGAGGAAGAAGCCCAGCCCCGCC
CTCCGCCCCTTCCGTCCCCACCCCATCCCGGCTCCCCAGGAGGCTCCCCGGCACTCCCTGTTCTCCTCGCTGGCGCTGCCTCTCCGACTCACTGCTC
GCCGGGCGCCGTCCGCCAGTCTCCCCGGGCCGGCGCTCCCTGCGGGGCCGGCGCTCCCTAAGGATGGTACTGATTTTCGCCGCCACAGGAGACCGGTCGGAGGCCGCCCCCGGCGGC

Met Arg Leu Ala Cys Leu Leu Leu Gly Cys Gly Tyr Leu Ala His Val Leu Ala
CTCGCCTCTCCTCCGAGCAGCCAGGCGCCTCGGGACGCG     ATG AGG ACC TTG GCT TGC CTG CTC CTC GGC TGC GGA TAC CTC GCC CAT GTT CTT GCC

Glu Glu Ala Glu Ile Pro Arg Glu Val Ile    Glu Arg Leu Ala Arg Ser Gln Ile His Ser Ile Arg Asp Leu Gln Arg Leu Leu Glu Ile
GAG GAA GCC GAG ATC CCC CGC GAG GTG ATC    GAG AGG CTG GCC CGC AGT CAG ATC CAC AGC ATC CGG GAC CTC CAG CGA CTC CTG GAG ATA

Asp Ser Val Gly Ser Glu Asp Ser Leu Asp    Thr Ser Leu Arg Ala His Gly Val His Ala Thr Lys His Val Pro Glu Lys Arg Pro Leu
GAC TCC GTA GGG AGT GAG GAT TCT TTG GAC    ACC AGC CTG AGA GCT CAC GGG GTC CAT GCC ACT AAG CAT GTG CCC GAG AAG CGG CCC CTG

Pro Ile Arg Arg Lys Arg Ser Ile Glu Glu    Ala Val Pro Ala Val Cys Lys Thr Arg Thr Val Ile Tyr Glu Ile Pro Arg Ser Gln Val
CCC ATT CGG AGG AAG AGA AGC ATC GAG GAA    GCT GTC CCC GCT GTC TGC AAG ACC AGG ACC GTC ATT TAC GAG ATT CCT CGG AGT CAG GTC

Asp Pro Thr Ser Ala Asn Phe Leu Ile Trp    Pro Pro Cys Val Glu Val Lys Arg Cys Thr Gly Cys Cys Asn Thr Ser Ser Val Lys Cys
GAC CCC ACG TCC GCC AAC TTC CTG ATC TGG    CCG CCG TGC GTG GAG GTG AAA CGG TGC ACC GGC TGC TGC AAC ACG AGC AGT GTC AAG TGC

Gln Pro Ser Arg Val His His Arg Ser Val    Lys Val Ala Lys Val Glu Tyr Val Arg Lys Lys Pro Lys Leu Lys Glu Val Gln Val Arg
CAG CCC TCC CGC GTC CAC CAC CGC AGC GTC    AAG GTG GCC AAG GTG GAA TAC GTC AGG AAG AAA CCA AAA TTA AAA GAA GTC CAG GTG AGG

Leu Glu Glu His Leu Glu Cys Ala Cys Ala    Thr Thr Ser Leu Asn Pro Asp Tyr Arg Glu Glu Asp Thr Gly Arg Pro Arg Glu Ser Gly
TTA GAG GAG CAT TTG GAG TGC GCC TGC GCG    ACC ACA AGC CTG AAT CCG GAT TAT CGG GAA GAG GAC ACG GGA AGG CCT AGG GAG TCA GGT

Lys Lys Arg Lys Arg Lys Arg Leu Lys Pro Thr    oc
AAA AAG CGG AAA AGA AAG AGG TTA AAA CCC ACC    TAA  AGCAGCCAACCAGATGTGAGGTGAGGATGAGGCCAGCCCAGCCCTTTCCTGGGACATGGATGCATGGCGTGTTA

CATTCCTGAACCTACTACTGTACGGTGCTTATTGCCAGTGTGCCGGTCGTTGTTCTTCCTCCGTGAAAACTGTGTCCGAGAACACTCGGGAGAACAAAGAGAACAGAGACAGTGCACATTTGTTTAAT
GTGACATCAAAGCAAGTATTGTAGCACTCGGTGAAGCAGTAAGAAGCTTCCTTGTCAAAAGAGAGAGAGAAAGAGAAAAGAAAAAAAAGGAATTC

Translated Mol. Weight = 24046.60

FIG. I

Sequence of the Human Platelet-Derived Growth Factor A-Chain Clone Uppsala-13-1

```
GAATTCGTCCGCAAATATGCAGAATTACCGGCCGGGTCGCTCCTGAAGCCAGCCGGGAGGAGGCGGGGAACGCACCGAGGAAGAAGCCCAGCCCCGCC
CTCGCCCCTTCCGTCCCACCCCATCCGGGCGGCCCAGGAGGCTCCCGCGCTGCCGCGCACTCCTGTTCTCCTCCTGGCGCTGCCTCTCCGCACTCACTGCTC
GCCGGGGCCGTCCGGTCCCCAAGCTCCGTCCCCCGGCCACCCTCCTCCGGGCGCTCCTCCTGGGACAGGAGACCGGCTGGAGCGCCGCCCCGCGGC
CTCGCCTCTCCTCCGAGCAGCCAGCGCCTCGGGACGCG
                                    1
                                    Met Arg Thr Leu Ala Cys Leu Leu Leu Gly Cys Gly Tyr Leu Ala His Val Leu Ala
                                    ATG AGG ACC TTG GCT TGC CTG CTG CTC CTC GGA TAC CTC GCC CAT GTT CTG GCC
                                                    10                                              20
Glu Glu Ala Glu Ile Pro Arg Glu Val Ile Glu Arg Leu Ala Arg Ser Gln Ile His Ser Ile Arg Asp Leu Gln Arg Leu Leu Glu Ile
GAG GAA GCC GAG ATC CCC CGA GAG GTG ATC GAG AGG CTG GCC CGC AGT CAG ATC CAC AGC ATC CGG GAC CTC CAG CGA CTC CTG GAG ATA
            30                                             40                                              50
Asp Ser Val Gly Ser Glu Asp Ser Leu Asp Thr Ser Leu Arg Ala His Gly Val His Ala Thr Lys His Val Pro Glu Lys Arg Pro Leu
GAC TCC GTA GGG AGT GAG GAT TCT TTG GAC ACC AGC CTG AGA GCT CAC GGG GTC CAT GCT ACT AAG CAT GTG CCC GAG AAG CGG CCC CTG
            60                                             70                                              80
Pro Ile Arg Arg Lys Arg Ser Ile Glu Glu Ala Val Pro Ala Val Cys Lys Thr Arg Thr Val Ile Tyr Glu Ile Pro Arg Ser Gln Val
CCC ATT CGG AGG AAG AGA AGC ATC GAG GAA GCT GTC CCC GCT GTC TGC AAG ACC AGG ACG GTC ATT TAC GAG ATT CCT CGG AGT CAG GTC
            90                                            100                                             110
Asp Pro Thr Ser Ala Asn Phe Leu Ile Trp Pro Pro Cys Val Glu Val Lys Arg Cys Thr Gly Cys Cys Asn Thr Ser Ser Val Lys Cys
GAC CCC ACG TCC GCC AAC TTC CTG ATC TGG CCC CCG TGT GTG GAG GTG AAA CGG TGC ACC GGC TGT TGC AAC ACG AGC AGT GTC AAG TGC
           120                                            130                                             140
Gln Pro Ser Arg Val His His Arg Ser Val Lys Val Ala Lys Val Glu Tyr Val Arg Lys Lys Pro Lys Leu Lys Glu Val Gln Val Arg
CAG CCC TCC CGC GTC CAC CAC CGC AGC GTC AAG GTG GCC AAG GTG GAA TAC GTC AGG AAG AAG CCA AAA TTA AAA GAA GTC CAG GTG AGG
           150                                            160                                             170
Leu Glu Glu His Leu Glu Cys Ala Cys Ala Thr Thr Ser Leu Asn Pro Asp Tyr Arg Glu Glu Asp Thr Asp Val Arg OP
TTA GAG GAG CAT TTG GAG TGT GCC TGC GCC ACA ACC AGC CTG AAT CCG GAT TAT CGG GAA GAG GAC ACG GAT GTG AGG TGA GGATGAGCCGCA
           180                                            190                          196
GCCCTTTCCTGGGACATGGATGTATACATTCCTGAACCTACTATGTACGGTGCTTTATTGCCAGTGTGCGGTCTCTTTGTTCTCTCCGTGAAAAACTGTGTCCGAGAACAC
TCGGGAGAACAAAGAGACAGTGCACATTTGTTTAATGTGACATCAAAGCAAGTATTGTAGCACTCGGTGAAGCAGTAAGAAGCTTCCTTGTCAAAAGAGAGAGAGAAAGAAAAAAA
AAGGAATTC
```

Translated Mol. Weight = 22256.17

FIG. 2

Sequence of SV40 early promoter, polylinker, and SV40
poly A addition region from pSV7d

```
        1/2 PVUII site SV 40 early promoter -->
     CTGTGGAATGTGTGTCAGTTAGGGTGTGGAAAGTCCCCAGGCTCCCCAGCAGGCAGAAGT
     GACACCTTACACACAGTCAATCCCACACCTTTCAGGGGTCCGAGGGGTCGTCCGTCTTCA 61  ATGCAAAGCATGCATCTCAATTAGTCAGCAAGGAAAGTCCCCAGGCTCCCCAGCAGGCAG
     TACGTTTCGTACGTAGAGTTAATCAGTCGTTCCTTTCAGGGGTCCGAGGGGTCGTCCGTC
     68 SPHI 121  AAGTATGCAAAGCATGCATCTCAATTAGTCAGCAACCATAGTCCCGCCCCTAACTCCGCC
     TTCATACGTTTCGTACGTAGAGTTAATCAGTCGTTGGTATCAGGGCGGGGATTGAGGCGG
     132 SPHI 181  CATCCCGCCCCTAACTCCGCCCAGTTCCGCCCATTCTCCGCCCCATGGCTGACTAATTTT
     GTAGGGCGGGGATTGAGGCGGGTCAAGGCGGGTAAGAGGCGGGGTACCGACTGATTAAAA
     223 NCOI, 241  TTTTATTTATGCAGAGGCCGAGGCCGCCTCGGCCTCTGAGCTATTCCAGAAGTAGTGAAG
     AAAATAAATACGTCTCCGGCTCCGGCGGAGCCGGAGACTCGATAAGGTCTTCATCACTTC
     263 BGLI
                  |-polylinker->                              OC  OP OP
301  AGGCTTTTTTGGAGGAGATCGAATTCCCGGGTCTAGAGGATCCGTCGACCTAGATAAGTA
     TCCGAAAAAACCTCCTCTAGCTTAAGGGCCCAGATCTCCTAGGCAGCTGGATCTATTCAT
     321 ECORI, 326 SMAI XMAI, 332 XBAI, 338 BAMHI, 344 SALI 361  ATGATCATAATCAGCCATATCACATCTGTAGAGGTTTTACTTGCTTTAAAAAACCTCCCA
     TACTAGTATTAGTCGGTATAGTGTAGACATCTCCAAAATGAACGAAATTTTTTGGAGGGT
     362 BCLI, 405 DRAI, 421  CACCTCCCCCTGAACCTGAAACATAAAATGAATGCAATTGTTGTTGTTAACTTGTTTATT
     GTGGAGGGGGACTTGGACTTTGTATTTTACTTACGTTAACAACAACAATTGAACAAATAA
     466 HPAI 481  GCAGCTTATAATGGTTACAAATAAAGCAATAGCATCACAAATTTCACAAATAAAGCATTT
     CGTCGAATATTACCAATGTTTATTTCGTTATCGTAGTGTTTAAAGTGTTTATTTCGTAAA
                          End of SV40---> ||-pBR322 (pos. 4210)>
541  TTTTCACTGCATTCTAGTTGTGGTTTGTCCAAACTCATCCGCTCATGAGACAATAACCCT
     AAAAGTGACGTAAGATCAACACCAAACAGGTTTGAGTAGGCGAGTACTCTGTTATTGGGA
```

RECOMBINANT PDGF A-CHAIN HOMODIMERS AND METHODS OF USE

This application is a continuation of pending prior U.S. application Ser. No. 08/260,203, filed Jun. 8, 1994, which is a continuation of U.S. application Ser. No. 07/942,379, filed Sep. 9, 1992, which is a continuation of U.S. application Ser. No. 07/633,671, filed Dec. 26, 1990, which is a divisional of U.S. application Ser. No. 07/574,540, filed Aug. 27, 1990, now issued of U.S. Pat. No. 5,219,759, which is a continuation of U.S. application Ser. No. 07/041,299, filed Apr. 22, 1987.

TECHNICAL FIELD

The invention is in the fields of biochemistry, molecular biology, and genetic engineering. More particularly it relates to the identification and isolation of genes for human platelet-derived growth factor (PDGF) A-chain polypeptides and precursor, polypeptides, recombinant vectors for cloning and expressing those genes in prokaryotic or eukaryotic hosts, methods for producing recombinant PDGF A-chain polypeptides, and PDGF comprised of recombinant PDGF A-chain polypeptides.

BACKGROUND

PDGF is the major mitogen in serum for mesenchymal-derived cells. PDGF is stored in platelet α-granules and released locally during platelet activation when blood vessels are injured. PDGF is a potent chemoattractant for monocytes and neutrophils and for fibroblasts and smooth muscle cells. These activities make PDGF an important component in tissue repair processes.

Purified native PDGF is a glycoprotein of approximately 30,000 daltons and is composed of two disulfide-linked chains. There are two types of chains, designated A and B. Whether native PDGF is a hetecodimer, a mixture of homodimers or a mixture of heterodimer and homodimer(s) is not known, but the dimer structure is functionally important, since reduction irreversibly destroys the biological activity of PDGF.

The B-chain is derived by proteolytic processing of a 241 amino acid precursor. The B-chain precursor is encoded by the c-sis gene, the cellular counterpart to the transforming gene v-sis of simian sarcoma virus (SSV), cDNA encoding the B-chain has been reported previously in Nature (1985) 316:748–750. There is homology between the B-chain and the transforming protein v-sis. The cloning and expression of the v-sis gene is described in EPA 85112852.0 (publication no. 0177957). Studies of v-sis indicate that B-chain homodimers have mitogenic activity. Also, sequencing of porcine PDGF has revealed that it contains only one type of chain, corresponding to human B-chain (EMBO J (1984) 3:2963–2967).

Johnsson, A., et al, EMBO J (1984) 3:921–928 describe a partial amino acid sequence for PDGF A-chain. See also Nature (1983) 304: 35–39 and Science (1983) 221: 275–277. Heldin, C. H, et al, Nature (1986) 319:511–514 describes an osteosarcoma-derived growth factor (ODGF) that is structurally related to putative PDGF A-chain homodimer. The studies of ODGF suggest that PDGF A-chain homodimer would exhibit biological activity.

DISCLOSURE OF INVENTION

The present invention is based on the isolation of cDNAs encoding two forms of PDGF A-chain precursors, the preparation of vectors for cloning and expressing PDGF A-chain polypeptides, and the expression of biologically active PDGF A-chain proteins using such expression vectors.

Accordingly, one aspect of the invention is recombinant DNA encoding a PDGF A-chain polypeptide.

Cloning and expression vectors containing such recombinant DNA are another aspect of the invention.

Hosts such as transformed yeast and mammalian cells which contain such expression vectors and are capable of producing biologically active (as measured by the assay described in §5 of the examples) recombinant PDGF comprised of PDGF A-chain polypeptides are another aspect of the invention.

Methods for producing biologically active PDGF A-chain proteins which employ such hosts are still another aspect of the invention.

Recombinant PDGF comprised of PDGF A-chain polypeptide is a further aspect of the invention.

BRIEF DESCRIPTION OF THE DRAWINGS

FIG. 1 shows the nucleotide sequence and deduced amino acid sequence of one form of PDGF A-chain precursor (designated D1).

FIG. 2 shows the nucleotide sequence and deduced amino acid sequence of a second form of PDGF A-chain precursor (designated 13-1).

FIG. 7 is the nucleotide sequence of the SV40 region used to make plasmid pSV7d described in the examples.

MODES FOR CARRYING OUT THE INVENTION

1. Definitions

Figure 3:
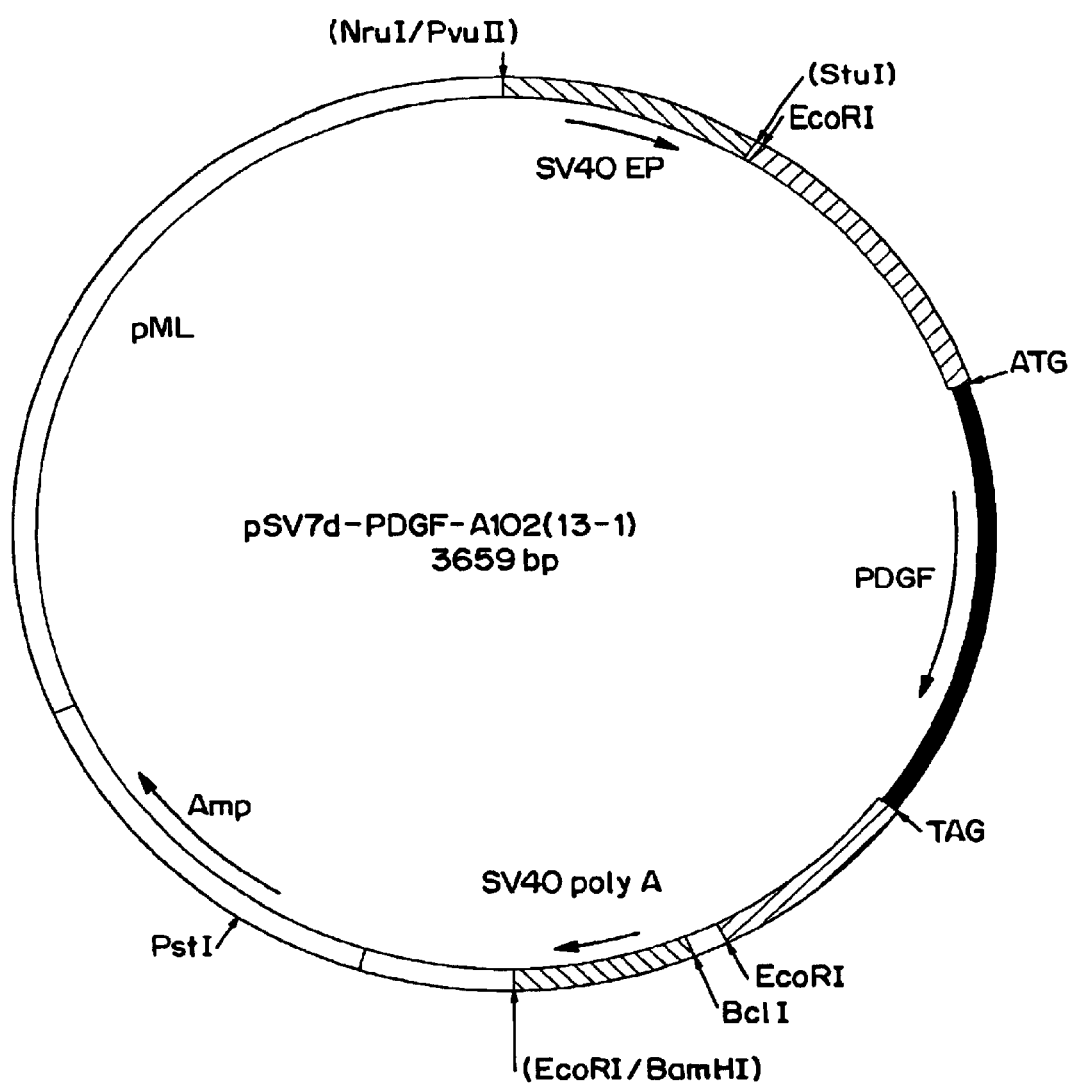
FIG. 3 is a diagram of plasmid pSV7d-PDGF-A102 (13-1) described in the examples.
Figure 4:
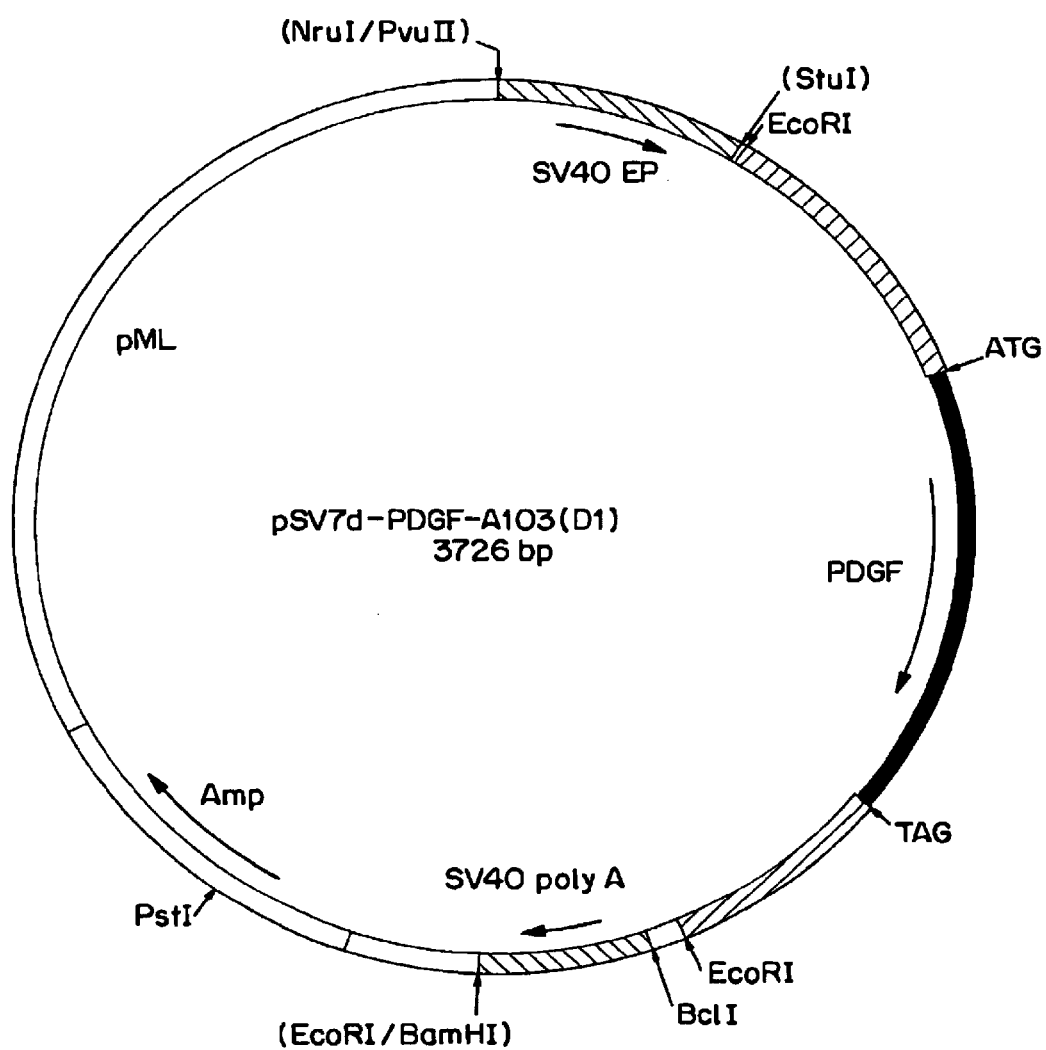
FIG. 4 is a diagram of plasmid pSV7D-PDCF-A103 (D1) described in the examples.
Figure 5:
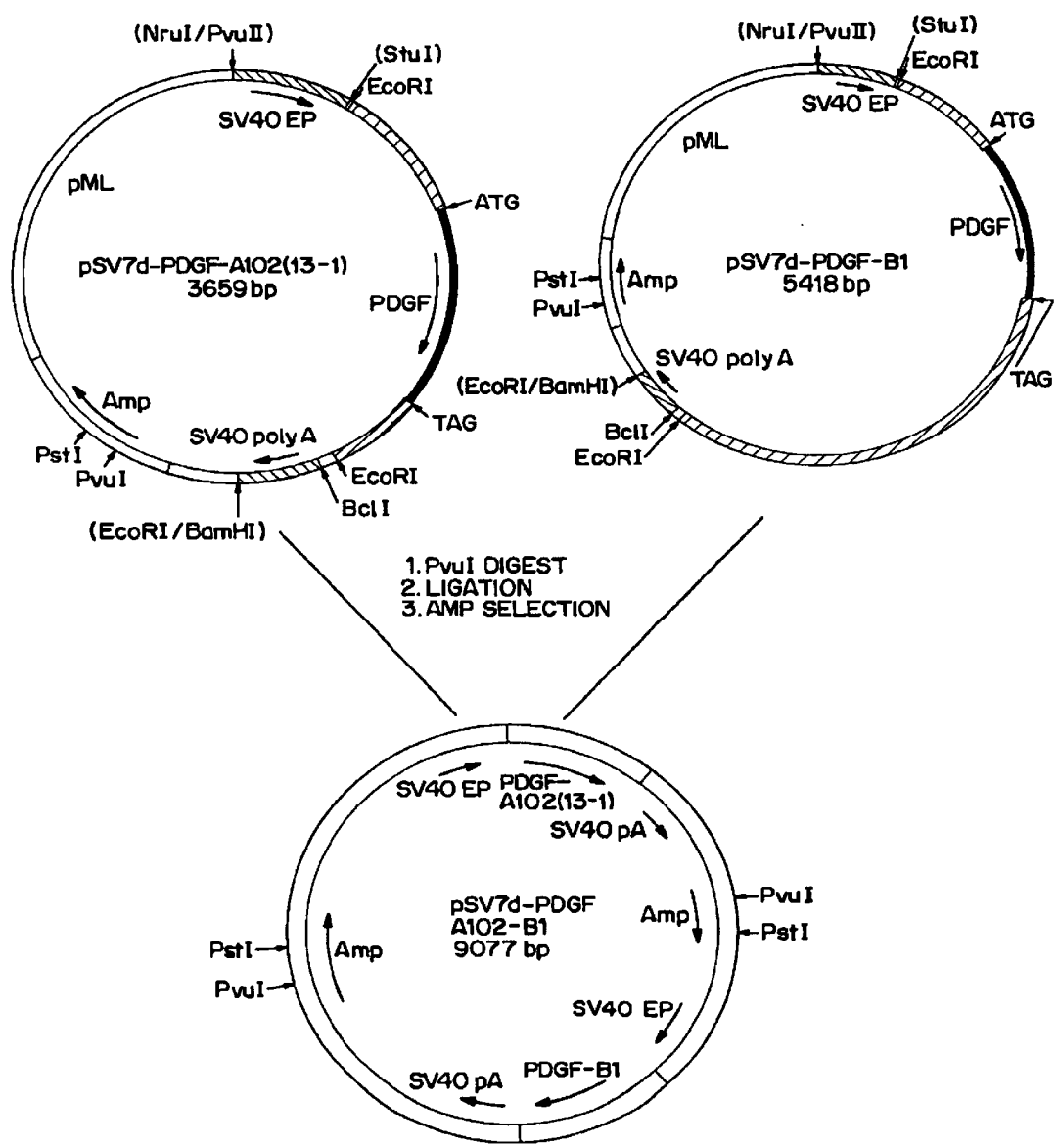
FIG. 5 is a diagram illustrating the scheme used to produce chimeric plasmid pSV7d-PDGF A102-B1 described in the examples.
Figure 6:
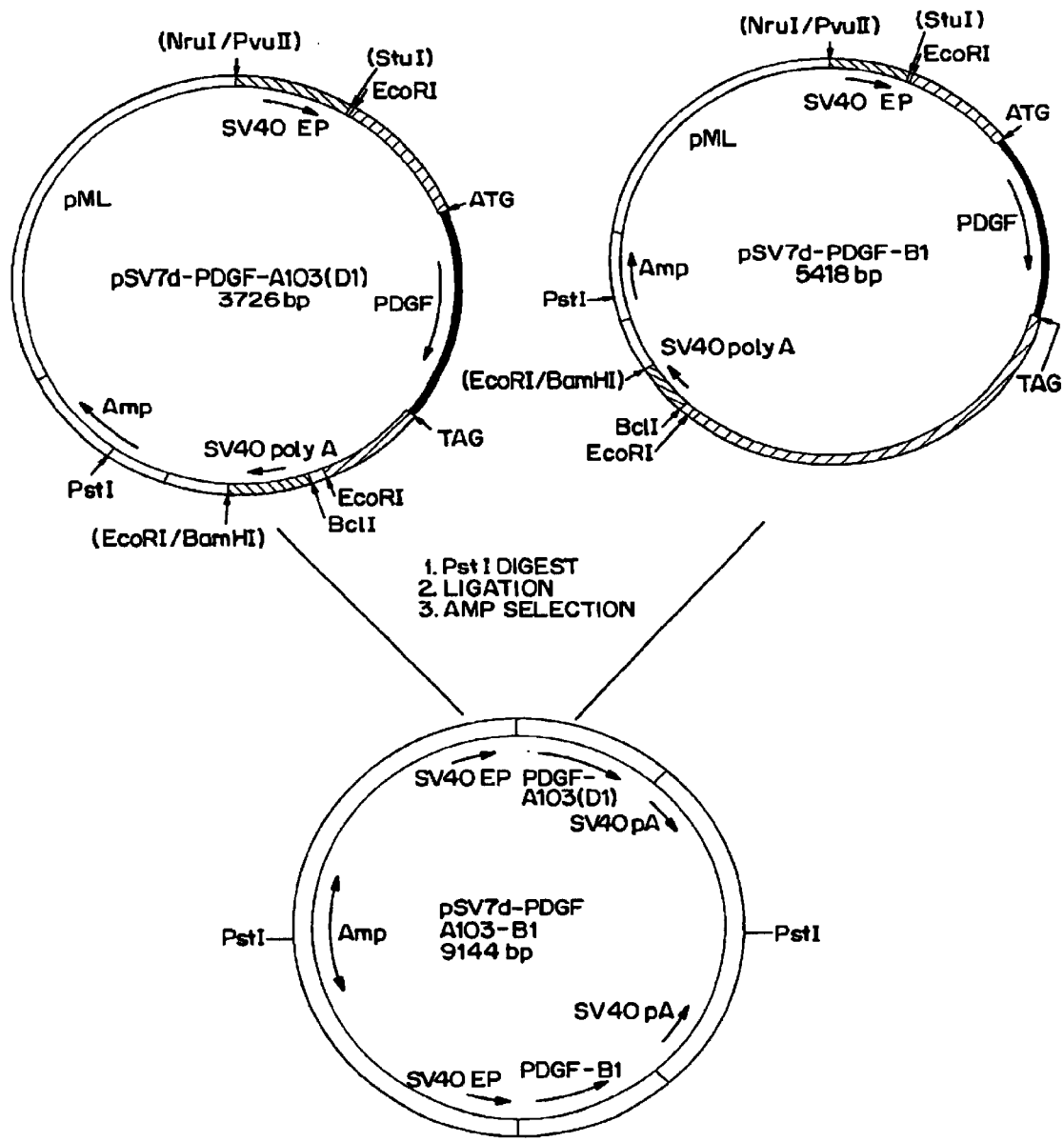
FIG. 6 is a diagram illustrating the scheme used to produce chimeric plasmid pSV7d-PDGF A103-B1 described in the examples.

The term "recombinant" as used herein to characterize DNA encoding PDGF A-chain polypeptides intends DNA of genomic, cDNA, semisynthetic, or synthetic origin which, by virtue of its origin or manipulation is (1) not associated with all or a portion of the DNA with which it is associated in nature or in the form of a library and/or (2) linked to DNA other than that to which it is linked in nature.

A "replicon" is any genetic element (e.g., a plasmid, a chromosome, a virus) that behaves as an autonomous unit of polynucleotide replication within a cell; i.e., capable of replication under its own control.

A "vector" is a replicon in which another polynucleotide segment is attached, so as to bring about the replication and/or expression of the attached segment. An "expression vector" refers to a vector capable of autonomous replication or integration and contains control sequences which direct the transcription and translation of the PDGF A-chain DNA in an appropriate host.

A "coding sequence" is a polynucleotide sequence which is transcribed and/or translated into a polypeptide.

A "promoter sequence" is a DNA regulatory region capable of binding RNA polymerase and initiating transcription of a downstream (i.e., in the 3' direction) coding sequence.

A coding sequence is "under the control" of the promoter sequence in a cell when transcription of the coding sequence results from the binding of RNA polymerase to the promoter sequence: translation of the resulting mRNA then results in the polypeptide encoded within the coding sequence.

"Operably linked" refers to a juxtaposition wherein the components are configured so as to perform their usual function. Thus, control sequences operably linked to a coding sequence are capable of effecting the expression of the coding sequence.

"control sequences" refers to those sequences which control the transcription and/or translation of the coding sequence(s): these may include, but are not limited to, promoter sequences, transcriptional initiation and termination sequences, and translational intitiation and termination sequences. In addition, "control sequences" refers to sequences which control the processing of the polypeptide encoded within the coding sequence; these may include, but are not limited to sequences controlling secretion, protease cleavage, and glycosylation of the polypeptide.

"Transformation" is the insertion of an exogenous polynucleotide into a host cell. The exogenous polynucleotide may be maintained as a plasmid, or alternatively, may be integrated within the host genome.

2. Recombinant PDGF A-Chain DNA

The recombinant PDGF A-chain DNA of the invention encodes at least amino acids 87–193, inclusive of the boxed amino acid sequence shown in FIG. 1 and analogs of that amino acid sequence which are substantially homologous and functionally equivalent thereto. The term "substantially homologous" intends that the number of amino acid variations (including substitutions and/or deletions) in said sequence be less than about 10, preferably less than about 3. The term "functionally equivalent" intends that the sequence of the analog defines a chain that will produce a protein having the biological activity of PDGF (as measured by the assay described in §5 of the examples). The DNA may include in addition DNA encoding one or more of amino acid residues 194–196, inclusive of the boxed sequences of FIG. 1 or 2, DNA encoding one or more of amino acid residues 197–211, inclusive, of the boxed sequence shown in FIG. 1 and/or DNA encoding all or a portion of amino acids 1–86, inclusive of the boxed amino acid sequence shown in FIG. 1. A preferred DNA sequence encoding said amino acids 87–193 for expression in mammalian systems is the DNA sequence shown in FIG. 1. For expression in other organisms, it may be desirable to use sequences that employ codons preferred by the particular host in which the DNA is expressed.

The recombinant PDGF A-chain DNA may be genomic, cDNA or synthetic DNA. By way of example, the sequences shown in FIGS. 1 and 2 were obtained from a cDNA library prepared from mRNA of a PDGF-producing cell line. The library was probed with two probes having sequences based on the reported partial amino acid sequence of PDGF A-chain. Clones that hybridized to both probes provided the illustrated sequences. Those sequences may be used to probe human genomic libraries to obtain analogous genomic DNA encoding PDGF A-chain polypeptides. Based on the amino acid sequence deduced from the illustrated sequences, synthetic genes encoding PDGF A-chain polypeptides may be prepared in vitro by synthesizing individual overlapping complementary oligonucleotides and filling in single stranded nonoverlapping portions using DNA polymerase in the presence of the deoxyribonucleotide triphosphates.

The deduced amino acid sequence shown in FIG. 1 differs from the reported partial amino acid sequence derived by amino acid sequencing PDGF A-chain at amino acids 119, 141 and 143. The reported residues at those positions were assigned Val, Arg and Thr, respectively. As shown in FIG. 1, the PDGF A-chain cDNA indicates these residues are instead Ile. Gln, and Ser, respectively.

3. Cloning of PDGF A-Chain DNA

The PDGF A-chain DNA can be cloned into any suitable replicon to create a vector, and thereby be maintained in a composition which is substantially free of vectors that do not contain the PDGF A-chain gene (e.g., other clones derived from the library). Numerous cloning vectors are known to those of skill in the art, and the selection of an appropriate cloning vector is a matter of choice. Examples of vectors for cloning and host cells which they can transform include the bacteriophage λ (*E. coli*), pBR 322 (*E. coli*), pACYC 177 (*E. coli*), pKT 230 (gram-negative bacteria), pGV1106 (gram-negative bacteria), pLAFR1 (gram-negative bacteria), pME290 (non-*E. coli* gram-negative bacteria), pHV 14 (*E. coli* and *Bacillus subtilis*), pBD9 (*Bacillus*), pIJ61 (*Streptomyces*), pUC6 (*Streptomyces*), actinophage φC31 (*Streptomyces*, YIp5 (*Saccharomyces*, YCp19 (*Saccharomyces*, and bovine papillona virus (mammalian cells).

4. Expression of PDGF A-Chain DNA

The polynucleotide sequence encoding the PDGF A-chain polypeptide is expressed by inserting the sequence into an appropriate replicon thereby creating an expression vector, and introducing the resulting expression vector into a compatible host.

In creating an expression vector the sequence encoding the PDGF A-chain polypeptide is located in the vector with the appropriate control sequences. The positioning and orientation of the coding sequence with respect to the control sequences is such that the coding sequence is transcribed under the control of the control sequences: i.e., the promoter will control the transcription of the mRNA derived from the coding sequence; and the ribosomes will bind at the ribosomal binding site to begin the translational process; and the stop codon used to terminate translation will be upstream from the transcriptional termination codon. Commonly used prokaryotic control sequences include such commonly used promoters as the β-lactamase (penicillinase) and lactose (lac) promoter systems (Chang et al. Nature (1977) 198:1056) and the tryptophan (trp) promoter system (Goeddel et al, Nucleic Acids Res (1980) 8:4057) and the lambda-derived $P_L$ promoter and N-gene ribosome binding site (Shimatake et al, Nature (1981) 292:128). Control sequences for yeast vectors include promoters for the synthesis of glycolytic enzymes (Hess et al. J Adv Enzyme Reg (1968) 7:149; Holland et al, Biochemistry (1978) 17:4900). Additional promoters known in the art include the promoter for 3-phosphoglycerate kinase (Hitzeman et al, J Biol Chem (1980) 255:2073). Other promoters, which have the additional advantage of transcription controlled by growth conditions and/or genetic background are the promoter regions for alcohol dehydrogenase 2 (ADH2), isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequences in yeast-derived genes. Expression vectors for mammalian cells such as VERO, Hela or CHO cells, ordinarily include promoters and control sequences compatible with such cells as, for example, the commonly used early and late promoters from Simian Virus 40 (SV40) (Fiers et al, Nature (1978) 273:113), or other viral promoters such as those derived from polyoma. Adenovirus 2, bovine papilloma virus, or avian sarcoma viruses. The controllable promoter, hMTII (Karin, M., et al, Nature (1982) 299:797–802) may also be used.

In addition to control sequences, it may be desirable to add regulatory sequences which allow for regulation of the expression of the PDGF A-chain gene relative to the growth of the host cell. Examples of regulatory systems are those which cause the expression of a gene to be turned on or off in response to a chemical or physical stimulus, including the presence of a requlatory compound. In prokaryotic systems these would include the lac and trp operator systems. In eukaryotic systems induction can occur in methallothionein genes with heavy metals and the Mouse Mammary Tumor Virus (MMTV) system with steroids. In these cases, the sequence encoding the PDGF A-chain polypeptides would be placed in tandem with the regulatory element.

There are also selective elements which give rise to DNA amplification which in turn can result in higher levels of specific protein production, in eukaryotic systems these include the dihydrofolate reductase gene (dhfr) which is amplified in the presence of methotrexate, and adenosine deaminase (ADA) in the presence of deoxycorfomycin. In these cases the sequence encoding the PDGF A-chain polypeptides may either be present on the same plasmid or merely be cotransfected together with the selectable element to allow for integration within the host cell genome near each other.

Other typ s of regulatory elements may also be present in the vector, i.e., those which are not necessarily in tandem with the sequence encoding PDGF A-chain. An example is the SV40 enhancer sequence. which, by its mere presence, causes an enhancement of expression of genes distal to it.

Modification of the sequence encoding PDGF A-chain, prior to its insertion into the replicon, may be desirable or necessary, depending upon the expression system chosen. For example, in some cases, it may be necessary to modify the sequence so that it may be attached to the control sequences with the appropriate orientation, i.e., to maintain the reading frame. In some cases, it may be desirable to add sequences which cause the secretion of the polypeptide from the host organism, with subsequent cleavage of the secretory signal. The techniques for modifying nucleotide sequences utilizing cloning are well known to those skilled in the art. They include, e.g., the use of restriction enzymes, of enzymes such as Bal31 to remove excess nucleotides, and of chemically synthesized oligonucleotides for use as adapters, to replace lost nucleotides, and in site directed mutagenesis.

The appropriately modified sequence encoding the PDGF A-chain polypeptide may be ligated to the control sequences prior to insertion into a vector. Alternatively, the coding sequence can be cloned directly into an expression vector which already contains the control sequences and an appropriate restriction site. For expression of the PDGF A-chain polypeptide in prokaryotes and in yeast, the control sequences will necessarily be heterologous to the coding sequence. In cases where the PDGF A-chain gene is to be expressed in cell lines derived from vertebrates, the control sequences may be either heterologous or homologous, depending upon the particular cell line.

Depending on the host cell used, transformation is done using standard techniques appropriate to such cells. The calcium treatment employing calcium chloride, as described by Cohen, S. N., Proc Natl Acad Sci (USA) (1972) 69:2110, or the $RbCl_2$ method described in Maniatis et al, Molecular Cloning: A Laboratory Manual (1982) Cold Spring Harbor Press, p. 254 and Hanahan, D., J Mol Biol (1983) 166: 557–580 may be used for prokaryotes or other cells which contain substantial cell wall barriers. For mammalian cells without such cell walls, the calcium phosphate precipitation method of Graham and van der Eb, Virology (1978) 52:546, optionally as modified by Wigler, M., et al. Cell (1979) 16:777–785 may be used. Transformations into yeast may be carried out according to the method of Beggs, J. D., Nature (1978) 275:104–109 or of Hinnen, A., et al, Proc Natl Acad Sci (USA) (1978) 75:1929.

Transformed cells are then grown under conditions which permit expression of the PDGF A-chain gene and assembly of the expression product into a biologically active PDGF (i.e., into a dimeric form). As shown in the following experimental section, initial attempts to produce recombinant PDGF A-chain homodimers in bacteria produced little, if any, biologically active PDGF. This may be due to a variety of reasons, such as improper dimer formation or improper folding, in addition to producing recombinant PDGF A-chain homodimer, the present invention permits production of heterodimers of PDGF A-chain and PDGF B-chain by co-expressing the genes for both PDGF A-chain and PDGF B-chain through use of separate vectors or a single vector that contains an A-chain gene and the B-chain gene. The thus synthesized recombinant PDGF protein is then isolated from the host cells and purified. If the expression system secretes the PDGF into the growth media, the PDGF is isolated directly from the media. If the recombinant PDGF is not secreted, it is isolated from cell lysates. The selection of the appropriate growth conditions and recovery methods are within the skill of the art. With regard to purification, see for instance, EPA Publication No. 0177957 and Nature (1986) 319:511–514.

Use and Administration of Recombinant PDGF

Recombinant PDGF prepared according to the invention is generally applied topically to wounds such as cutaneous, dermal, mucosal, or epithelial wounds in vertebrates, particularly mammals including man, domestic and farm animals, sports animals and pets. It may be used to treat any type of full or partial thickness wounds including traumatic wounds, surgical wounds, thermal or chemical wounds (burns) radiation wounds, and ulcers such as decubiti and cutaneous ulcers caused by vascular, hematologic and metabolic diseases, infections, or neoplasms.

The PDGF may be formulated using available excipients and carriers in the form of a lotion, spray, gel, ointment or as a controlled or sustained release dosage form. Additional ingredients such as other growth factors (FGF, CTAP-III, EGF, IGF-1, IGF-2, TGF-β, TGF-α), buffers, local anesthetics, antibiotics, gelling agents, and the like may be included in the formulation.

For topical administration, which is the most appropriate with regard to cutaneous lesions, standard topical formulations are employed using, for example. 0.1–10% concentrations of PDGF are normally applied. Th concentration of formulation depends, of course, on the severity of the wound and nature of the subject. In some treatment regimens, the dose is lowered with time to lessen likelihood of scarring.

Controlled or sustained release formulations of recombinant PDGF are made by incorporating the PDGF in carriers or vehicles such as liposomes, nonresorbable semipermeable polymers such as ethylene-vinyl acetate copolymers and Hytrel® copolymers, swellable polymers such as hydrogels, or resorbable polymers such as collagen and certain polyacids or polyesters such as those used to make resorbable sutures to provide for sustained release of the PDGF to the wound site over an extended time period, typically from one day to one week. Such incorporation may be particularly desirable when the PDGF is incorporated into a wound dressing. The mechanism of PDGF release from the formulation may be diffusion, osmosis, leaching, dissolution, erosion, or combinations thereof. In diffusional sustained release formulations the PDGF dissolves in and diffuses through the carrier or vehicle on which it is encapsulated/dispersed. In leaching or dissolution formulations, the PDGF is leached from the carrier by body fluids. The concentration of polypeptide in the sustained release formulation will normally be at least 1 $\mu$g/ml, usually between 10 $\mu$g/ml and 10 mg/ml. In some instances it may be desirable to continually maintain the treatment composition at the affected area or wound site during the healing period. This may be achieved via a multiplicity of intermittent applications of the treatment composition, or by administering the PDGF via a sustained release dosage form such as those described above. In this regard, the term "continually" denotes true continuous administration such as is achieved by such sustained release dosage forms or that achieved by such repeated applications that provide a pharmacokinetic pattern that mimics that achieved by true continuous administration.

EXAMPLES

The following examples further describe the isolation of DNA encoding PDGF A-chain polypeptides and the expression of that DNA in various hosts to produce biologically active PDGF.

In the following, "digestion" refers to the enzymatic cleavage of DNA by restriction endonucleases. Restriction endonucleases commonly referred to as restriction enzymes are well characterized and commercially available and used in accordance with manufacturer's specifications. Digestion with restriction enzymes is frequently followed by treatment with alkaline phosphatase according to manufacturer's specifications to remove the terminal 5' phosphates, thus preventing self ligation of a vector having two compatible ends.

"Fill in" refers to the enzymatic process of creating blunt ends by repairing overhanging ends generated by certain restriction enzymes. The repair is a function of DNA polymerase I large fragment (Klenow) and deoxynucleotide triphosphates and is used according to manufacturer's specifications.

Gel isolation of a DNA restriction fragment refers to the recovery of a specific fragment, electrophoretically separated on, either an agarose gel or polyacrylamide gel (depending on size of fragment), by either electroelution or melting and extraction of gel slice.

All DNA manipulations are done according to standard procedures. See Maniatis et al. Molecular Cloning, Cold Spring Harbor Lab., 1982. All enzymes used are obtained from commercial sources and used according to the manufacturer's specifications.

1. Isolation and Characterization of PDGF A-Chain cDNA

A λgt10 cDNA library was constructed from poly (A)$^+$ RNA from the human clonal glioma cell line U-343 MGaCl2:6 using the LiCl/urea method modified as described by Betsholtz, C., et al, Cell (1984) 39:447–457. Oligo(dT)-primed synthesis of ds cDNA was performed according to Gubler, U., and Hoffman. B. J., Gene (1983) 25:263–299. The resulting cDNA was treated with T4 DNA polymerase and subcloned into EcoRI-cleaved λgt10 using EcoRI linkers. The recombinant phage were plated in E. coli C600hfl.

Two oligonucleotide probes, designated PDGF-A-1 and PDGF-A-2 were synthesized based on the known partial amino acid sequence of PDGF A-chain. Both were made using solid-phase phosphoramidite methodology. The double-stranded probe PDGF-A-1 was synthesized as two overlapping 50-bp oligonucleotides and radiolabeled Using [$\alpha$-$^{32}$P]-deoxynucleoside triphosphates and Klenow fragment of DNA polymerase I. PDGF-A-2 was synthesized as a 37-base template and a 12-base complementary primer and was radiolabeled as PDGF-A-1. The nucleotide sequences (single strand) of the two probes are given below.

PDGF-A-1 (86-mer)
   CCATCGAGGAGGCCGTGCCTGCAGTGTGC
   AAGAACCCGCACCGTGATCTATGAGATCCCCCG
   CTCC
   CAGGTCGACCCCACCTCCGCC PDGF-A-2 (37-mer)
   AAGCGCTGCACCGGCTGCTGCAACACCAGCAGC
   GTGA These probes were used to screen the library (2×10$^6$ clones). Duplicate nitrocellulose filter lifts were hybridized with the probes at 42° C., in 20% formamide, 5×SSC, 50 mM sodium phosphate pH 7.0, 5× Denhardt's, 0.10% SDS, 200 $\mu$g/ml sonicated salmon sperm DNA and washed in 0.5×SSC, 0.1% SDS at 42° C. Clones D1 and 13-1 were selected from among those that hybridized to both probes and sequenced by dideoxy nucleotide chain termination after subcloning into M13 phage derivatives. Partial nucleotide sequences of D1 and 13-1 are shown in FIGS. 1 and 2.

The longest open reading frame of D1 predicts a PDGF A-chain precursor of 211 amino acids (shown in FIG. 1); the boxed portion designates the 125-amino acid PDGF A-chain polypeptide.

The deduced amino acid sequence of FIG. 1 matches the reported partial sequence of the PDGF A-chain obtained by amino acid sequencing except at amino acids 119, 141, and 143, found to be Ile, Gln, and Ser, respectively, instead of the previously assigned Val, Arg, and Thr. The ATG codon at amino acid position 1 precedes a basic amino acid (Arg) followed by 18 hydrophobic residues. This is characteristic of a signal peptide sequence and is consistent with the observation that PDGF A-chain homodimers produced by human osteosarcoma cells are secreted. Comparison with preferred signal peptidase cleavage sites suggests that processing may occur between amino acids Ala20 and Glu21. The N-terminal sequence of platelet PDGF A-chain is found at amino acid 87, indicating that a propeptide of 66 amino acids (44% charged residue) is cleaved from the precursor to generate a 125-amino-acid A-chain protein. This cleavage occurs after a run of four basic amino acids, Arg-Arg-Lys-Arg. Additional proteolytic processing may occur in the C-terminal region.

The corresponding open reading frame of 13-1 (FIG. 2) predicts a PDGF A-chain precursor of 196 amino acids identical in sequence to the precursor of D1 but lacking 15 C-terminal residues. Again, the mature polypeptide is boxed in FIG. 2.

cDNA for PDGF B-chain was isolated from the same cDNA library for use in the following experiments in which D1, 13-1, and B-chain cDNA were cloned in an analogous manner.

2. Mammalian Cell Expression

In order to establish a permanent cell line producing PDGF, the entire cDNA was cloned into a mammalian cell expression vector which contains a transcriptional regulatory element, a polyadenylation site, and a transcriptional terminator signal. The resulting plasmid along with a selectable marker was introduced into Chinese hamster ovary cells (CHO).

2.1. Constructions of Mammalian Cell Expression Vectors pSV7d-PDGF-A102, pSV7d-PDGF-A103, and PSV7d-PDGF-B1

Three separate mammalian cell expression vectors were constructed by isolating EcoRI fragments from each of the three cDNA clones and ligating them into pSV7d (see §2.4 below) previously digested with EcoRI and treated with alkaline phosphatase. The resulting clones pSV7d-PDGF-A103 (D1), pSV7d-PDGF-A102 (13-1), and pSV7d-PDGF-B1 (B-chain) were isolated and characterized by r striction digests. These plasmids were used to produce the chimeric plasmids pSV7d-PDGF A102-B1 and pSV7d-PDGF A103-B1 for coexpression of B-chain and A-chain. Large-scale plasmid preparations were carried out for all of the constructions described. The DNA was used to transfect CHO cells.

2.2. CHO Cell Transfections

Transfections were performed as follows:

CHO dhfr⁻ cells (Urlaub and Chasin, Proc. Natl Acad Sci USA (1980) 77:4216) were plated at a density of $5 \times 10^5$ to $10^6$ cells per 10 cm dish the day prior to transfection in nutrient medium (F12 supplemented with 1.18 mg/ml Na$_2$CO$_3$, 292 µg/ml glutamine, 110 µg/ml sodium pyruvate, 100 U/ml penicillin, 100 U/ml streptomycin, 200 µg/ml proline, and 10% FCS). The CHO cells were transfected with each of the pSV7d-PDGF expression plasmids that were mixed with plasmid pAD-dhfr which bears a selectable marker (a dhfr gene driven by the adenovirus major late promoter, see below), using a modification of the procedure described by Graham and van der Eb, Virology (1973) 52:456–467. The samples, containing a total of 10 µg of plasmid DNA, were added to the dishes and allowed to settle onto the cells in a carbon dioxide incubator (37° C.). Six hours later, the supernatants were aspirated, the cells rinsed gently with Ca and Mg-free phosphate-buffered saline (PBS-CMF), and the dishes exposed to 15% glycerol as an adjuvant for 3.5–4 min. The cells were then rinsed gently and fed with the above-described medium.

Forty-eight hours after the addition of DNA to the cells, the cells were split 1:20 into selective medium (DMEM supplemented with a 1:1 mixture of fetal calf serum and dialyzed fetal calf serum in addition to the components described above). After growth in selective medium for 1–2 weeks, colonies appeared and were isolated and grown individually. Assays for PDGF were performed on each of the clones (as described below).

Transfections in which pSV7d-PDGF-A103 plus pSV7d-PDGF-B1 and pSV7d-PDGF-A102 plus pSV7d-PDGF-B1 are coprecipitated were also performed in addition to transfections with the chimeric plasmids described in §2.1 in order to establish cell lines that are producing PDCF as a heterodimer of A-chain and B-chain.

The plasmid pAD-dhtr, bearing the mouse dihydrofolate reductase (dhfr) gene was constructed by fusing the major late promoter from adenovirus-2 (Ad-MLP, map units 16–17.3) to the mouse dhfr cDNA (Subramani et al. J Mol Cell Biol (1982) 1:584–864) at the 5' end. DNA coding for the intron for SV40 small t antigen and the SV40 early region polyadenylation site was obtained from pSV2-neo (Southern and Berg, J Mol Appl Genet (1982) 1:327–341), and fused to the 3' end of the dhfr cDNA. These three segments were subcloned into pBR322 to obtain the plasmid pAD-dhfr.

Several of the primary CHO transfected cell lines secreted PDGF into the medium at levels of 1–2 ng/ml/24 hr as determined by the mitogen assay described in §5.

Several primary clones from each of the transfected lines were selected for amplification in increasing amounts of methotrexate, 0.05 and 0.1, and 1.0 µM concentrations. Amplification and selection of methotrexate-resistant colonies were performed according to Kaufman, R. S., and Sharp, P. A., J Mol Biol (1982) 159:601–621.

2.3. Results of PDGF Expression

Results of PDGF expression from CHO cells are summarized in Table 1 below. Media from CHO cell lines transfected with PDGF expression plasmids were assayed by the PDGF mitogen assay described in §5. The results of these experiments indicate that the PDGF A-chain homodimer is active.

TABLE 1

CHO Cells Transfected with PDGF Expression Plasmids:
Level of Active PDGF Secreted into Media

| Cell Lines | Plasmid | Level of PDGF/24 hr |
|---|---|---|
| EXPERIMENT 1 | | |
| Primary Cell Lines | PSV7d-PDGF-A102 | 1–2 ng/ml |
| | pSV7d-PDGF-A103 | no cells survived |
| | pSV7d-PDGF-B1 | 1–2 ng/ml |
| Amplified cell lines methotrexate level: 0.1 µM | pSV7d-PDGF-A102 | 50–100 ng/ml |
| | p5V7d-PDGF-B1 | 100–150 ng/ml |
| Methotrexate level: 1 µM | pSV7d-PDGF-A102 | 50–100 ng/ml |
| | pSV7d-PDGF-B1 | 100–150 ng/ml |
| EXPERIMENT 2 | | |
| Primary Cell Lines | pSV7d-PDGF-A102 | 10–20 ng/ml |
| | pSV7d-PDGF-A103 | 1–2 ng/ml |
| | pSV7d-PDGF-B1 | 10–20 ng/ml |
| | pSV7d-PDGF-A102 + pSV7d-PDGF-B1 | 1–2 ng/ml |
| | pSV7D-PDGF-A103 + pSV7d-PDGF-B1 | 1–2 ng/ml |
| Amplified Cell lines methotrexate level: 1 µM & 2 µM | No increase in level of PDGF secreted into media. | |
| EXPERIMENT 3 | | |
| Primary Cell Lines | pSV7D-PDGF A102-B1 | 40 ng/ml |
| | pSV7D-PDGF A103-B1 | no secretion detected |

2.4. Construction of PSV7d

Figure 8:
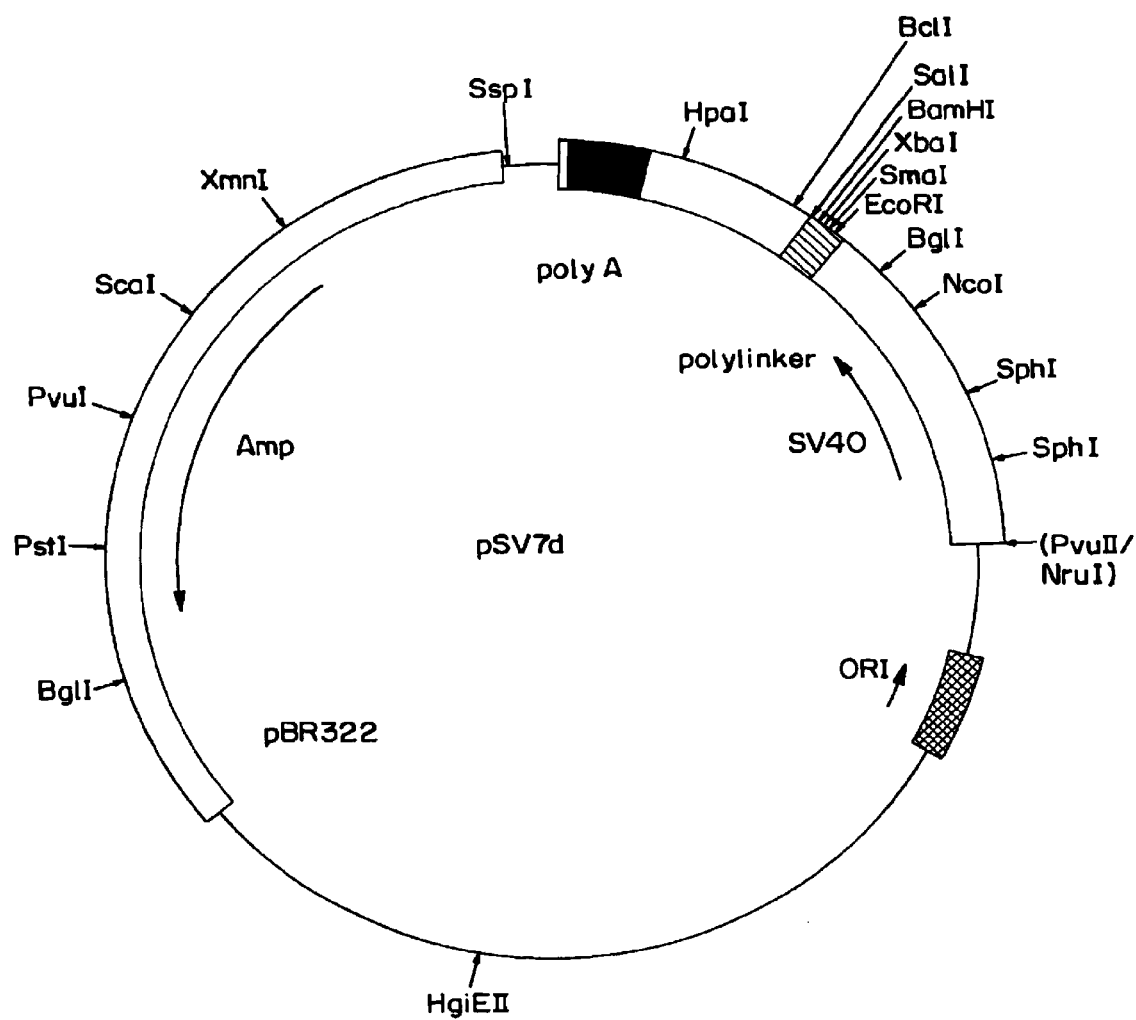
FIG. 8 is a map of the plasmid pSV7d described in the examples.
Figure 9:
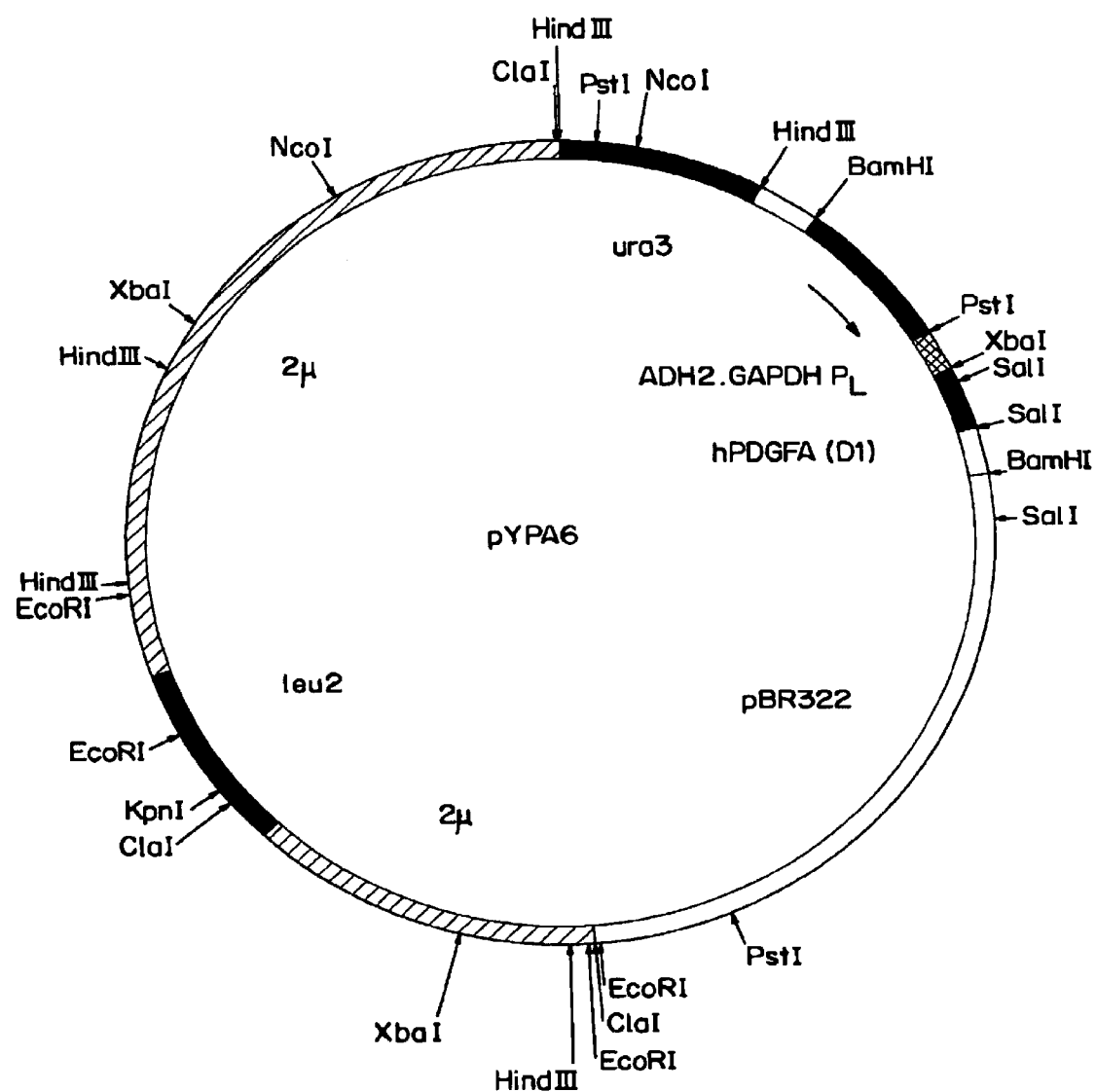
FIG. 9 is a map of the plasmid pYpA6 described in the examples (§3.1.2).
Figure 10:
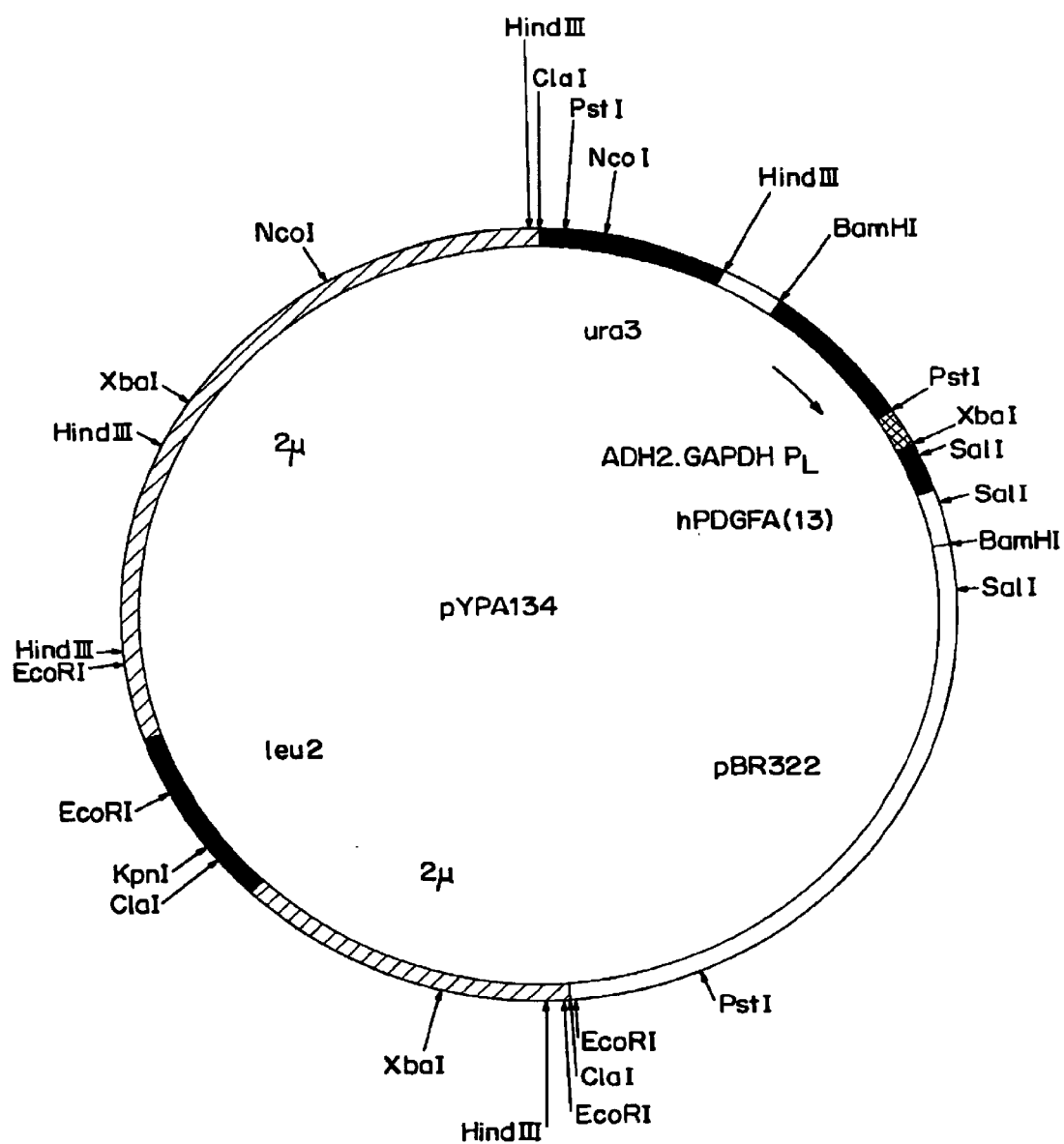
FIG. 10 is a map of the plasmid pYpA134 described in the examples (§3.1.2).
Figure 11:
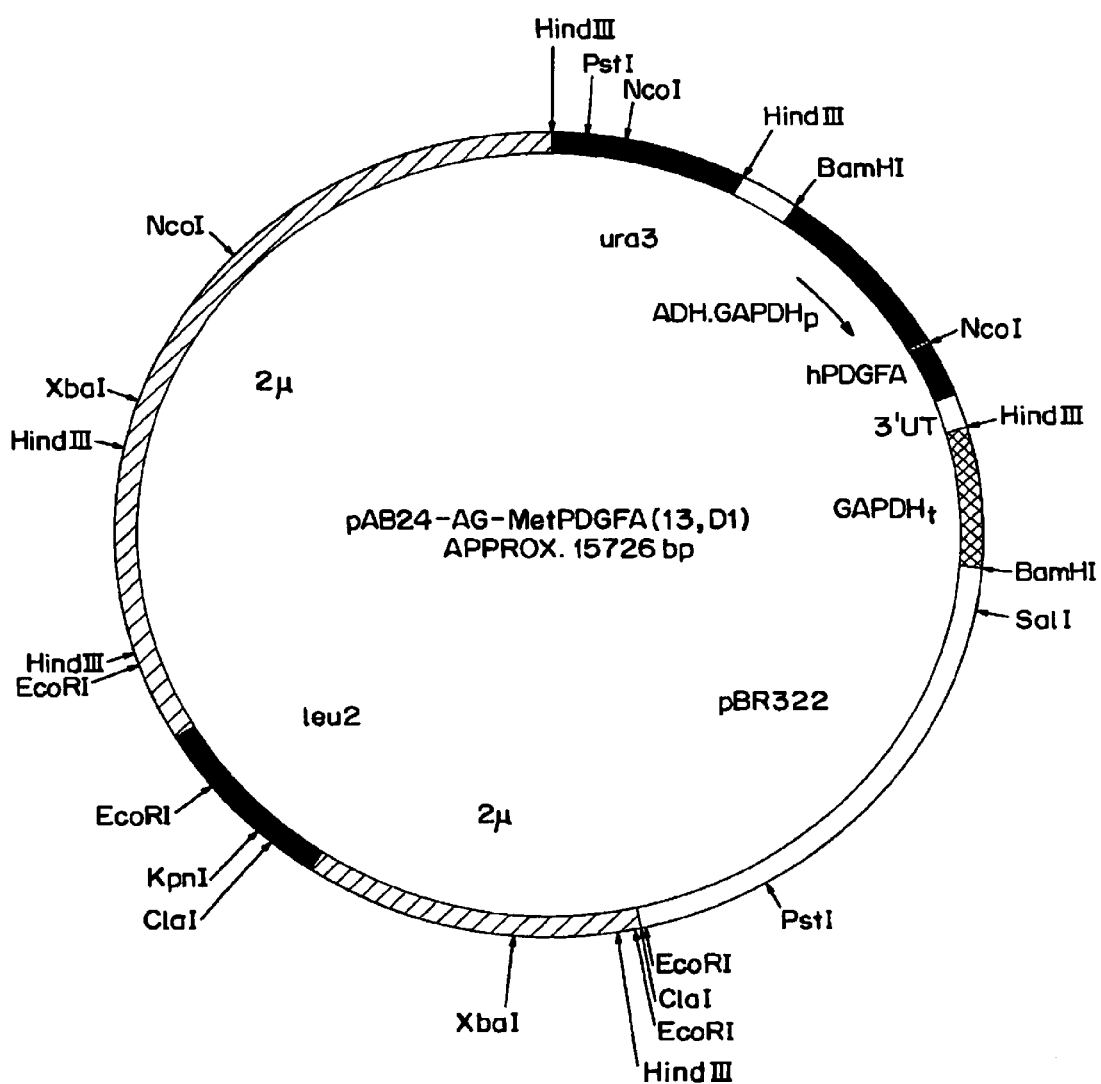
FIG. 11 is a map of the plasmids pAB24-AGMetPDGFAD1/A13.1 described in the examples (§3.2.2).
Figure 12:
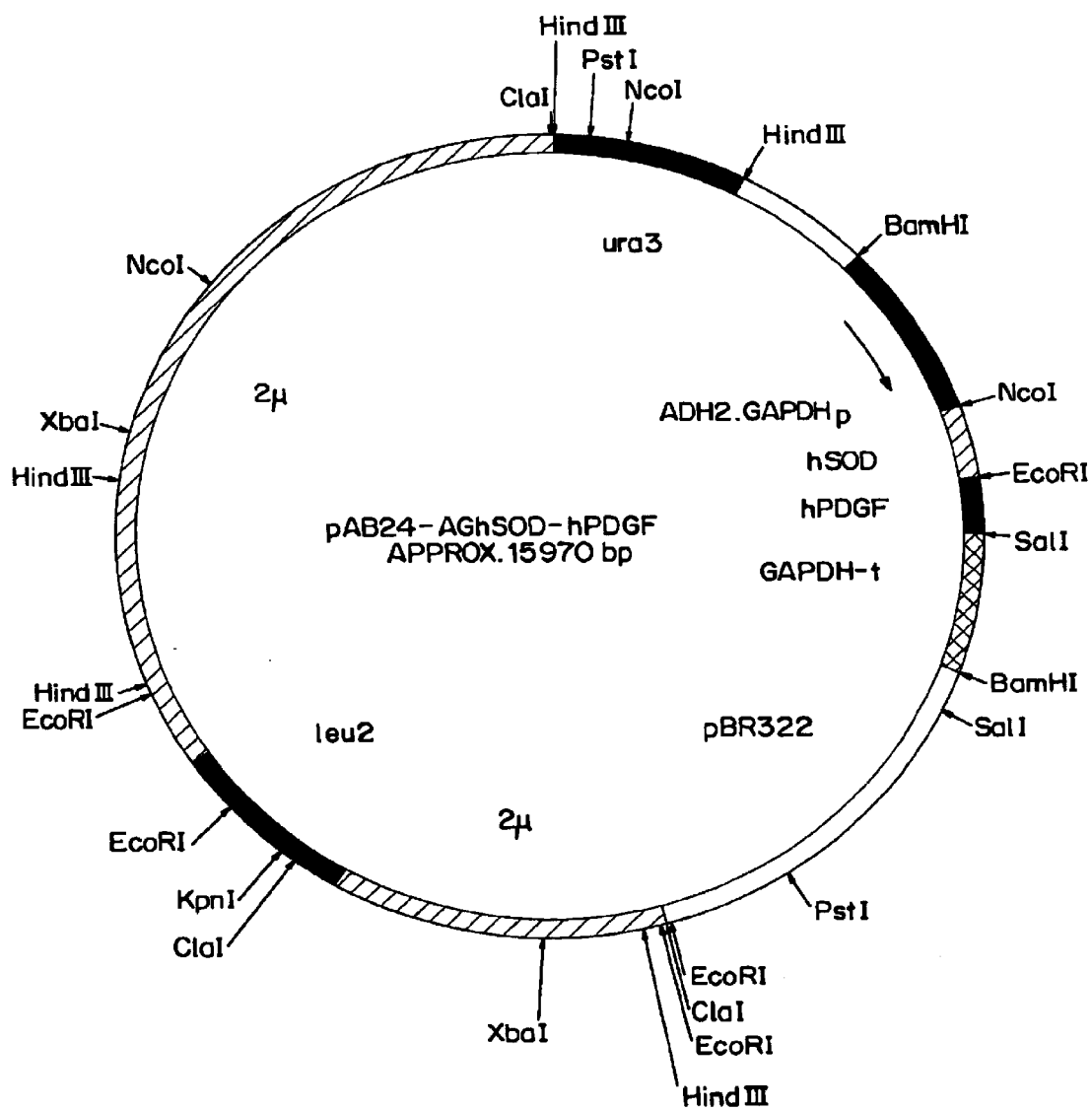
FIG. 12 is a map of the plasmids pAB24-AGhSODhPDGF AD1/13.1 described in the examples (§3.3.2).
Figure 13:
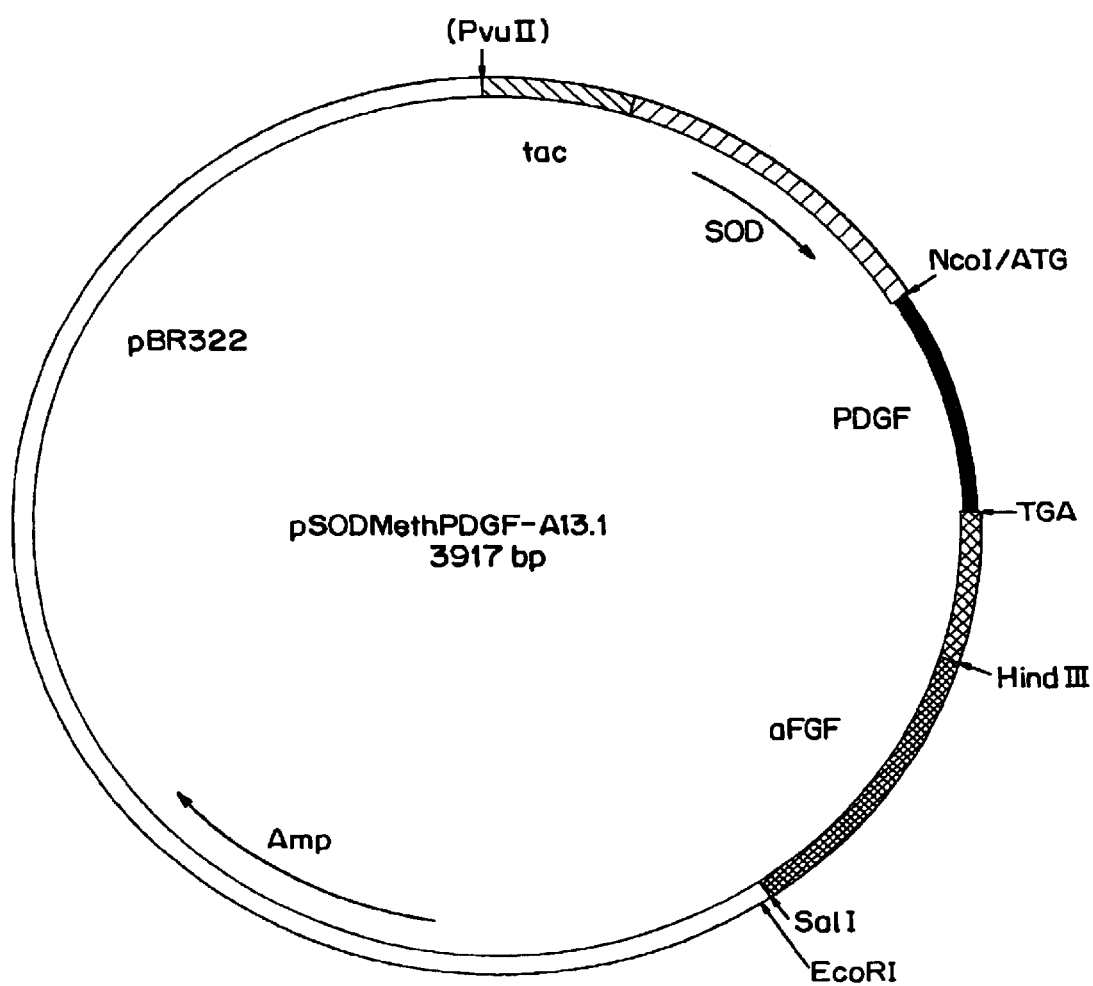
FIG. 13 is a map of the plasmid pSOD-MethPDGF-A13.1 described in the examples (§4.2).
Figure 14:
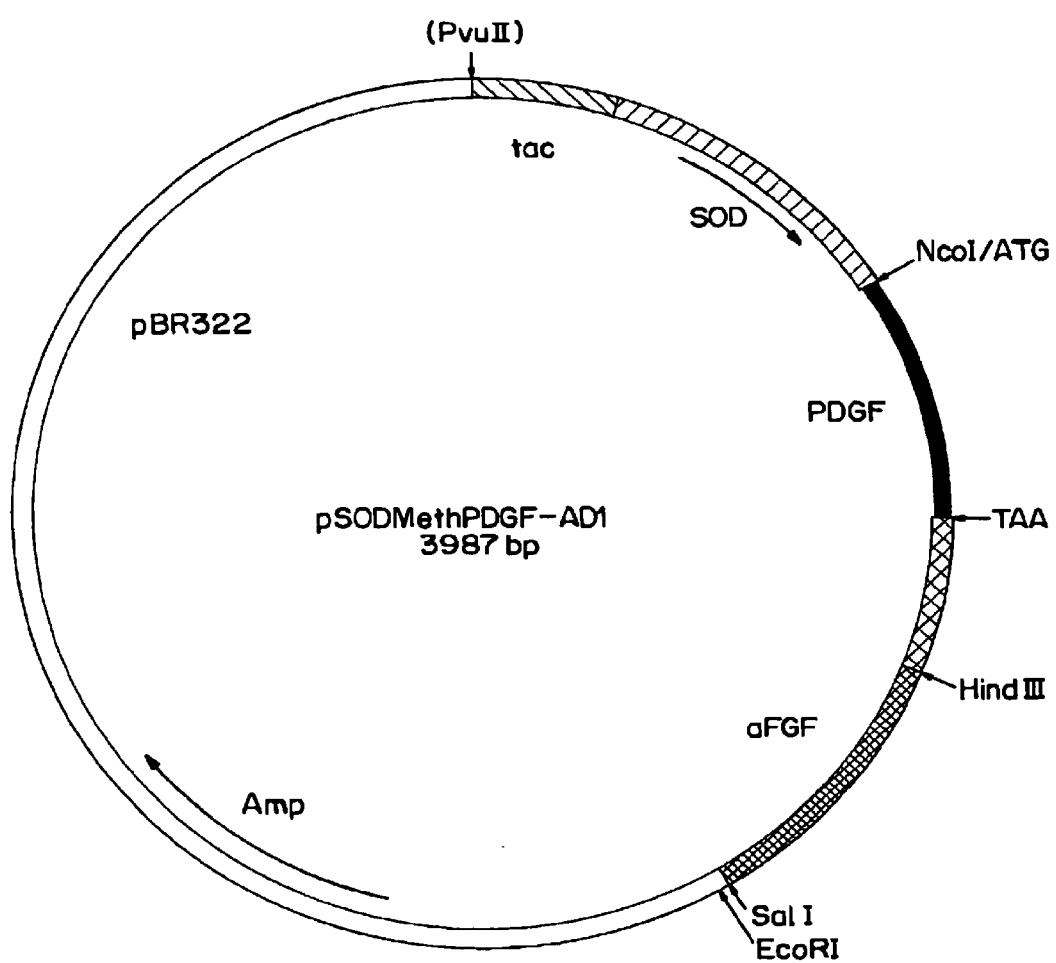
FIG. 14 is a map of the plasmid pSOD-MethPDGF-AD1 described in the examples (§4.2).

The mammalian cell shuttle vector plasmid pSV7d contains the SV40 origin of replication and early promoter (315 bp, PvuII pos 272-StuI pos 5193 with an 8 bp deletion between nucleotides 173 and 182), a polylinker, and the SV40 poly A addition site (217 bp, BclI pos 2775-pos 2558). Buchman, L., et al. "The SV40 Nucleotide Sequence" pp 799–841 DNA TUMOR VIRUSES Second Edition edited by Tooze, J. The sequence of the SV40 region is shown in FIG. 7. The SV40 sequences were cloned into the pBR322 derivative pML (Lusky and Botchan. (1984) Cell 36:391) between nucleotide 4210 and NruI pos 973. Maniatis, T., et al "Nucleotide Sequence of pBR322" (1983) Molecular Cloning: A Laboratory Manual. The SV40 sequences are positioned such that the direction of transcription from the early promoter is in the same direction as the ampicillin gene of the vector. A map of the plasmid is shown in FIG. 8.

3. Yeast Expression

Due to the ability of yeast to secrete and process proteins, the genes for the mature PDGF A-chains and B-chain were fused with the sequence of the α-factor leader, a yeast secretory signal sequence which would allow for secretion of PDGF. Yeast transformed with these plasmids would be expected to synthesize a protein containing an NH$_2$-terminal α-factor leader and COOH-terminal PDGF chain separated by Lys-Arg. Since this molecule is targeted for secretion, cleavage after the processing site Lys-Arg by the yeast should result in secretion of the mature growth factor. Lys-Arg is the processing site used by the natural prepro-PDGF, as well as the prepro-α-factor.

3.1. Regulatable Secretion in Yeast

PDGF B-chain protein, and the two forms of the A-chain protein, D1 and 13-1, are produced and secreted by yeast strain *Saccharomyces cerevisiae* AB110 (Mata, ura 3–52, leu 2–04, or both leu 2–3 and leu 2–112, pep 4–3, his 4,580, cir°) transformed with yeast expression plasmids pYpNB4, pYpA6, and pYpA134 respectively. The plasmids contain the sequence coding for their respective mature PDGF protein along with pBR322 sequences including the origin of replication and the ampicillin resistance gene, as well as yeast sequences including the 2-micron and selectable markers leu and ura genes. Expression of the mature PDGF genes is under the control of the regulatable promoter ADH2-glyceraldehyde-3-phosphate-dehydrogenase (GAPDH) and α-factor terminator (see §3.1.4).

3.1.1. Construction of pYpNB4: A Yeast Expression Vector for PDGF B-Chain

The entire gene coding for the mature PDGF B-chain was synthesized by automated oligonucleotide synthesis on a silica support as described by Urdea et al. Proc Natl Acad Sci USA (1983) 80:7461–7465, using N,N-diisopropyl phosphoramidites. Yeast-preferred codons were used. The synthetic gene was cloned as a 350-bp XbaI-SalI fragment into pAG (see §3.1.4), which was digested with XbaI and SalI and gel isolated to give pAGSB-4.

The expression cassette containing the synthetic PDGF B-chain gene was cut out as a BamHI fragment and cloned into the yeast shuttle vector pAB24 (see §3.1.4), previously digested with BamHI and treated with alkaline phosphatase, to give pYpNB4.

3.1.2. Construction of pYpA6 and pYpA134: Yeast Expression Vectors for PDGF A-Chain In vitro mutagenesis was used to generate XbaI and SalI sites at the end of the two different mature PDGF A-chain genes in order to clone the genes into pAG (see §3.1.4). In vitro mutagenesis was performed according to the procedure of Zoller and Smith. DNA (1984) 3(6):479–488. A SacI-HindIII fragment, containing the entire coding region for the mature polypeptide, was cloned from each of the PDGF A-chain genes into M13mp19 in order to generate single-stranded template. The following synthetic oligonucleotides were used as mutagenic primers.

| Mutation | Sequence of Primer |
|---|---|
| 1. XbaI site at 5' end of 13-1 and D1 | CTGCCCATTCTAGATAAGAGAAGCATC |
| 2. SalI site at 3' end of clone D1 | CCCACCTAAAGTCGACTTCCAGATGTGAGG |
| 3. SalI site at 3' end of clone 13-1 | GATGACCCGTCGACCAATCCTGGGA |

Mutagenesis of clone D1 was carried out using, primers 1 and 2: primers 1 and 3 were used for clone 13-1. An approximately 400-bp XbaI-SalI (partial) fragment from clone D1 and an approximately 360-bp XbaI-SalI (partial) fragment from clone 13-1 were each isolated and cloned into pAG, which was digested with the XbaI and SalI and gel isolated, to give pAG-AD1 and pAG-A13.1, respectively. The expression cassettes containing the two forms of the mature PDGF A-chain gene were cut out as BamHI fragments and each cloned into pAB24, previously digested with BamHI and treated with alkaline phosphatase, to give plasmids pYpA6 and pYpA134.

3.1.3. Yeast Transformation and Expression

Yeast expression plasmids pYpNB4, pYpA6, and pYp134 were transformed into into yeast strain *S. cerevisiae* AB110 (Mata, ura 3–52, leu 2–04, or both leu 2–3 and leu 2–112, pep 4–3, his 4–580, cir°), as described by Hinnen et al (Proc Natl Acad Sci USA (1978) 75:1929–1933) and plated on ura⁻, 8% glucose, sorbitol plates. Transformants are grown in leu⁻, 8% glucose liquid medium for 24 hr and then plated onto leu⁻, 8% glucose sorbitol plates to get individual colonies. Individual colonies are picked and grown in 3 ml of leu⁻, 8% glucose medium for 24 hr at 30° C., and then inoculated (1:50) into 1 liter of ura⁻, 1% glucose media and grown for 75 hr at 30° C. Yeast culture medium was assayed for PDGF activity by the human foreskin fibroblast mitogen assay (see §5). The yeast transformant pYpNB4-2 secretes PDGF B-chain into the medium at a level of 500 ng/ml, transformant pYpA6-NT1 secretes PDGF A-chain (D1 form) into the medium at a level of 750 ng/ml and transformant pYpA134-NT1 secretes PDGF A-chain (13-1 form) into the medium at a level of 325 ng/ml.

Proteins from the above cultures were run on a 15% polyacrylamide SDS gel. The B-chain migrates at the expected size of 14.5 Kd. The 13.1 form of A-chain migrates as 2 bands at 18 and 18.5 Kd respectively. The size for the expected single species is 18 Kd. The D1 form of A-chain migrates as 3 bands at 19, 18.5 and 18 Kd. Its expected size on the same gel for a single species is calculated at 19.5 Kd. The extra bands for both A-chains are due to proteolytic cleavage at either the amino-terminus and/or the carboxy-terminus.

3.1.4. Plasmids Used for The Preparation of Yeast Expression Vectors pAG- is a general yeast expression cassette vector derived from pAG-TNF where pAG-TNF is only used for convenience of cloning with the pAG-construct being relevant to this application.

The expression cassette vector, pAG-TNF, contains the regulatable ADH2-GAPDH promoter, the α-factor leader, the synthetic TNF gene, and the α-factor terminator cloned in pBRΔRI-Sal. The ADH2-GAPDH promoter was isolated as a 1.0-Kbp BamHI-NcoI fragment from pAGΔXbaGAP1. The 5' end of the α-factor leader was supplied as a synthetic adaptor for the following sequence and having NcoI- and PstI-compatible overhangs:

CATGAGATTCCTTCAATTTTTACTGCA
TCTAAGGAAGTTAAAAATG

The 3' end of the α-factor leader, the synthetic TNF gene and the α-factor terminator was isolated as a PstI-BamRI fragment from pHG100-TNF. The three fragments were ligated together and cloned into pBRΔRI-Sal which had been previously digested with BamHI and treated with alkaline phosphatase, pERΔRI-Sal was constructed by digesting pBR322 with EcoRI and SalI, filling in the overhangs with Klenow fragment, and ligating on BamHI linkers. The vector and linkers were digested with BamHI and the BamHI-BamHI 3.8 kb vector was gel isolated and recircularized by self-ligation. The resulting plasmid was designated pBRΔRI-Sal.

The plasmid pAGAXbaGAP1 contains the ADH2-GAPDH hybrid promoter and the GAPDH terminator cloned into pBRΔRI-Sal. The ADH2-GAPDH promoter (the only sequence pertinent to this application) was isolated as a 1.1-kb BamHI-NcoI fragment from pJS103 (described below). In addition, an approximately 90-bp XbaI-XbaI deletion was introduced into the 5' end of the promoter fragment by cutting the plasmid with XbaI, filling in the overhang ends with Klenow fragment, and dNTPs and recircularizing the plasmid, thus giving pAGΔXbaGAP1.

pHG100-TNF contains the α-factor promoter, leader, and terminator with the synthetic gene coding for TNF inserted in frame at the 3' end of the leader. The 1.0 kb Pst-BamHI fragment isolated from this plasmid contains 240 bp of the 3' end of the α-factor leader, the 494-bp synthetic TNF gene (as an XbaI-SalI fragment) and the 272-bp α-factor terminator. The α-factor sequences which are the only sequences relevant to this application are derived from pAB114, pAB114 is described in EPO 0 116 201, pages 14–18, and Brake, A. J., et al, Proc Natl Acad Sci USA (1984), 81:4642–4646. The only difference is that a silent mutation was introduced by M13 mutagenesis to create an XbaI site at the 3' end of the leader to facilitate cloning of heterologous genes.

The comparison of the 3' end of the α-factor leader from the wild type (pAB114) versus the altered α-factor (pHG100) illustrated below shows that a silent mutation was incorporated to code for an XbaI site just 5' to the processing site (LysArg). This allows for insertion of heterologous genes without the "spacer" codons (must provide the LysArg processing site and maintain reading frame).

(Beier et al, Nature (1982) 300:724–728) with restriction enzyme EcoRV, which cuts at position +66 relative to the ATG start codon, as well as in two other sites in pADRZ, outside of the ADH2 region. The resulting mixture of a vector fragment and two smaller fragments was resected with Bal31 exonuclease to remove about 300 bp. Synthetic XhoI linkers were ligated onto the Bal31-treated DNA. The resulting DNA linker vector fragment (about 5 kb) was separated from the linkers by column chromatography, cut with restriction enzyme XhoI, religated, and used to transform E. coli to ampicillin resistance. The positions of the XhoI linker were determined by DNA sequencing. One plasmid which contained an XhoI linker within the 5' nontranscribed region of the ADH2 gene (position −232 from ATG) was cut with the restriction enzyme XhoI, treated with nuclease S1, and subsequently treated with the restriction enzyme EcoRI to create a linear vector molecule having one blunt end at the site of the XhoI linker and an EcoRI end. The GAP portion of the promoter was constructed by cutting plasmid pPGAP1 with the enzymes BamHI and EcoRI, followed by the isolation of the 0.4 Kbp DNA fragment. This purified fragment was then completely digested with the enzyme AluI and an approximately 200 bp fragment was isolated.

This GAP promoter fragment was ligated to the ADH2 fragment present on the linear vector described above to give plasmid pJS103.

pPGAP1 pPGAP1 is a yeast expression cassette vector which has a polyrestriction site linker between the GAPDH terminator and a truncated GAPDH promoter region. The polyrestriction site contains the recognition sites for NcoI, EcoRI, and SalI, and the cassette is excisable as a BamHI fragment. The preparation of pPGAP1 is described in EPO 0 164 556 and Travis, J., et al. J Biol Chem (1985) 260(7):4384–4389. In both references pPGAP1 is referred to pPGAP.

pAB24 is a yeast shuttle vector which contains the complete 2μ sequences (Broach, In: Molecular Biology of the Yeast Saccharomyces, 1:445, Cold Spring Harbor Press (1981)) and pBR322 sequences. It also contains the yeast URA3 gene derived from plasmid YEp24 (Botstein et al. Gene (1979) 8:17) and the yeast LEU2$^d$ gene derived from plasmid pC1/1 (described in European Patent Application

```
       α-factor leader       processing site      spacer     α-factor gene
       IleAlaAlalysGluGluGlyValSerLeuAspLysArgGlyAlaGluAlaTrpHisTrpLeuGlnLueGly
pA8114 ATTGCTGCTAAAGAAGAAGGGGTATCTTTGGATAAAAGAGAGGCTGAAGCTTGGCATTGGTTGCAACTGGGG XbaI                 HindIII
pHG100 ATTGCTGCTAAAGAAGAAGGGGTATCTCTAGATAAAAGAGCTCCAACCTCTTCCTCTACCAAGAAGACCCAG
       IleAlaAlsLysGluGluGlyValSerLeuAspLysArgAlaProThrSerSerSerThrLyslysThrGln
       α-factor leader       processing site   gene for IL-2
``` pJS103

Plasmid pJS103 contains the inducible hybrid ADH2-GAPDH promoter. The hybrid promoter is made up of the transcriptional and translational initiation region from the GAPDH promoter and is under the regulatory control of the ADH2 transcriptional regulatory region. The ADH2 transcriptional regulatory region is derepressed in the absence of a readily available source such as glucose (without exogenous inducer). By allowing for glucose exhaustion after the yeast culture is grown to high density, the transcriptional control region will be derepressed and expression of the desired peptide will occur.

Plasmid pJS103 was constructed as follows. The ADH2 portion of the promoter was constructed by cutting a plasmid containing the wild-type ADH2 gene from plasmid pADR2 publication no. EPO116201). Insertion of the expression cassette was in the BamHI site of pBR322, thus interrupting the gene for bacterial resistance to tetracycline.

3.2. Intracellular Expression in Yeast

PDGF B-chain and the two forms of the A-chain protein, D1 and 13.1, can be produced internally by yeast strain S. cerevisiae AB110 transformed with pAB24-AGMetPDGF-SB, pAB24-AGMetPDGF-AD1, and pAB24-AGMetPDGF-A13.1 respectively. The plasmids contain the sequence coding for their respective mature PDGF protein with an additional methionine at the amino terminus which allows for direct expression. Expression of the mature PDGF genes is under the control of the regulatable promoter ADH2-GAPDH and the GAPDH terminator.

3.2.1. Construction of PAB24-AGMetPDGF-SB: A Yeast Expression Vector for PDGF B-chain In order to express the mature B-Chain internally in yeast, plasmid pAGSB-4 (53.1.1) is digested with BqlII and then treated with S1 nuclease to remove the 5' overhang and generate a blunt end. A linker of the following sequence:

```
5'-GATCTATGTC-3'
    ATACAG
```

(which contains a BqlII overhang, a start codon, and regenerates the codon coding for the first amino acid, serine, of the mature PDGF B-chain) is ligated to pAGSB-4 and then the plasmid is digested with BqlII and SalI. The 345 bp BqlII-SalI fragment is gel isolated and ligated into BqlII and XhoI digested pRSP101 to generate plasmid pAB24-AGMetPDGF-SB.

The plasmid pRSP101 is a yeast expression vector containing the regulatable ADH2-GAPDH promoter and GAPDH terminator and was derived from pAB24 and pBS100. Plasmid pRSP100 was constructed by excising the BamHI cassette from pBS100 and ligating it into pAB24 which had been previously digested with BamHI and treated with phosphatase. The intermediate vector was then digested with NcoI and SalI, to remove the fragment between the promoter and the terminator, and then treated with S1 nuclease to remove the single-stranded overhangs and make the ends blunt. A linker of the following sequence:

```
5'-AGATCTCTTGCTCGAG-3'
   TCTAGAGAACGAGCTC
``` was then ligated in to add unique sites for BqlII and XhoI. Plasmid pBS100 is a yeast expression cassette vector cloned into a pBR322 derivative pAB12. The expression cassette contains the hybrid ADH2-GAPDH promoter and the GAPDH terminator flanking a gene segment from the HIV envelope gene. The ADH2-CAPDH prmoter is a 1200 bp BamHI-NcoI fragment isolated from pJS103 (§3.1.4) and the GAPDH terminator is a 900 by SalI-BamHI fragment isolated from plasmid pPGAP1 (§3.1.4). Plasmid pBS100 also contains a non-essential fragment between the NcoI and SalI sites which is replaced by gene fragments of interest. The xpression cassette can be removed from pBS100 by digestion with BamHI and cloned into yeast shuttle vectors for introduction into yeast cells.

Plasmid pAB12 is a pBR322 derivative lacking the region between the single HindIII and SalI sites and containing a BamHI linker inserted between the unique EcoRI site. This vector was constructed by digesting pBR322 to completion with HindIII and SalI followed by limited digestion wtih Bal31 nuclease, repair of the ends so created with the Klenow fragment of E. coli DNA polymerase I, and blunt-end ligation with T4 DNA ligase to reform closed covalent circles. The plasmid was the opened up with EcoRI, treated with the Klenow fragment of E. coli DNA polymerase I (to fill-in the 5' overhangs), blunt-end ligated with BamHI linkers, digested with BamHI to remove excess linkers, and then ligated to form closed circles.

3.2.2. Construction of pAB24-AGMetPDGF-AD1 and pAB24-AGMetPDGF-A13.1: Yeast Expression Vectors for PDGF A-Chain In order to clone the two mature A-chains of PDGF, to be expressed internally in yeast, the semisynthetic NcoI-HindIII fragments are isolated from the internal bacterial expression vectors pSOD-MethPDGF-AD1 and pSOD-MethPDGF-A13.1 (§4.2). These fragments contain the translational start codon ATG followed by the mature PDGF A-chain gene and the 3' untranslated region. The approximately 613 bp and 544 bp NcoI-HindIII fragments coding for D1 and 13.1 respectively are each ligated into pBS100 which is previously digested with NcoI and HindIII (cuts in the 5' end of the terminator region) to give the resulting plasmids pAGMetPDGF-AD1 and pAGMetPDGF-A13.1. The expression cassette containing the ADH2-GAPDH hybrid promoter, mature PDGF A-chain gene, and the GAPDH terminator is excised as a BamHI fragment and ligated into pAB24 which is previously digested with BamHI and treated with phosphatase to yield plasmids pAB24-AGMetPDGF-AD1 and pAB24-AGMetPDGF-A13.1.

3.2.3. Yeast Transformation and Expression

The yeast expression plasmids containing MetPDGF B-chain and two forms of A-chain: pAB24-AGMetPDGF-SB, pAB24-AGMetPDGP-AD1, and pAB24-AGMetPDGF-A13.1, were each transformed into yeast S. cerevisiae AB110 as described previously in §3.1.3.

3.3. Internal Expression as an SOD-fusion

3.3.1. Construction of PAB24-AGhSOD-hPDGF: A Yeast Expression Vector for an SOD-PDGF B-Chain Fusion Protein To make the above plasmid, the BqlII-SalI fragment encoding the mature PDGF B-chain is excised from pYpNB4. The following linker is ligated onto the 5' end:

```
5'-AATTCTAAAA
      GATTTTCTAG-3'
```

This linker includes a lys arg cleavage site for the Kex2 protease to allow separation of human superoxide dismutase (hSOD) and PDGF B-chain. The EcoRI-SalI fragment is then cloned into phosphatase-treated pSI4 (described in European Patent Application 86104066.5, publication no 0196056) digested with EcoRI and SalI. The BamHI cassette is then excised and subcloned into phosphatase-treated pAB24 digested with BamHI.

3.3.2. Construction of pAB24-AGSOD-hPDGF A (13.1 or D1): A Yeast Expression Vector for an SOD-PDGFA (13.1 or D1) Fusion Protein To make the above plasmid, the SalI fragments containing 102 and 87 of the N-terminal amino acids of mature PDGF A-chain forms D1 and 13.1 respectively are isolated. They are ligated to linkers that restore the first 23 amino acids of PDGF A-chain, introduce a lys arg (Kex2) cleavage site between SOD and PDGF, and an EcoRI restriction site at the 5' end.

```
5' AAT TCT AAA AGA TCT (sequence for next G
      GA TTT TCT AGA ZZ aa of         CAG CG
                     PDGF A-chain)

EcoRI      Lys Arg Ser                SalI
site           (1st aa in             site
               PDGF A-chain)
```

The EcoRI-SalI fragment (355 and 392 bp for clones 13.1 and D1 respectively) are then ligated into phosphatase treated pSI4 digested with EcoRI and SalI. The BamHI cassette is excised and subcloned into phosphatase-treated pAB24 digested with BamHI.

4. E. coli: Expression

In order to stabilize the expression of PDGF in E. coli, the gene for PDGF was fused 3' to the hSOD sequence which is expressed stably and in high levels in E. coli. To clone the gene for the mature PDGF A-chain (forms D1 and 13.1) and B-chain, the DNA sequences encoding the mature polypeptides were modified to include an NcoI site at the 5' end, this would result in a Methionine initiation codon in frame with the rest of the coding sequence.

4.1. Construction of pSOD-MethPDGF-SB: A Bacterial Expression Vector for PDGF B-chain The entire coding region for the PDGF B-chain was synthesized as described previously (§3.1.1) except that an NcoI site was generated at the 5' end instead of the XbaI site. The 350 bp NcoI-SalI PDGF B fragment was ligated into pSODCF2, digested previously with NcoI and SalI and gel isolated, to give plasmid pSOD-MethPDGF-SB.

pSODCF2 is an *E. coli* expression vector containing the TacI promoter (a hybrid trp-lac promoter) followed by a cDNA copy of the hSOD gene and a polylinker (for cloning COOH terminal fusions) cloned into pBR322, pSODCF2 is described in Steimer, K. S., et al, J Vicol (1986) 58:9–16.

4.2. Construction of pSOD-MethPDGF-AD1 and pSOD-MethPDGF-A13.1: Bacterial Expression Vectors for PDGF A-Chain In order to clone the two forms of the mature PDGF A-chain for *E. coli* expression the first 69 nucleotides were synthesized to include an NcoI site and code for a methionine at the 5' end and a SalI site at the 3' end. This fragment was ligated with each of the approximately 475-bp SalI HindIII fragment from clone 13-1 and the approximately 545 bp SalI-HindIII fragment from clone D1.

The resulting semisynthetic genes for both of the A-chains were cloned as NcoI-HindIII fragments into pbaFGF$_{Fix}$ which was previously digested with NcoI and HindIII and gel isolated to give pSOD-MethPDGF-AD1 and pSOD-MethPDGF-A13.1, respectively.

The plasmid pbaFGF$_{Fix}$ is plasmid pSODCF2 containing a 436-bp NcoI-SalI fragment coding for fibroblast growth factor (FGF) and was used only for convenience due to the presence of a HindIII site within the FGF sequences. Translation stop codons for PDGF are present, as evidenced by the sequence.

4.3. *E. coli*: Transformation and Expression

The *E. coli* expression plasmids pSOD-MethPDGF-AD1, pSOD-MethPDGF-A13.1, and pSOD-MethPDGF-SB were transformed into *E. coli* strain RRΔM15. Individual colonies were grown in L-broth medium with 100 μg/ml ampicillin and expression was induced as described by Hallewell, R. A., et al. Nucl Acid Res (1985) 13:2017–2034. The *E. coli* extracts were analyzed for PDGF activity. No activity was detected, although a protein of the expected size was found for the direct expression of form 13.1.

5. Bioassay for PDGF Activity 5.1. PDGF Produced in Mammalian Cells

Chinese hamster ovary cells (CHO) used in the process are normally grown in medium supplemented with 10% fetal calf serum (FCS). This presented a problem in assaying for PDGF due to the background contributed by the native bovine PDGF in FCS. Thus, it was necessary to devise culture conditions that support production of recombinant products while reducing the background. Using CHO cells transfected with the human β-interferon gene, it was found that expression levels reached approximately 50% of those observed in 10% FCS with culture medium supplemented by 5% platelet-deficient horse plasma (PDHS). This medium, when added to either the cell growth or mitogen assays, gave no background.

CHO transformants were assayed by adding 10 μl of a 24-hr supernatant harvest in 5% PDHS (and necessary dilutions, usually serial twofold and threefold) to the well of a 96-well plates of the assay.

5.2. PDGF Produced in Yeast

Samples of supernatants of yeast which had expressed PDGF were appropriately diluted, depending upon expected activity, and then serially diluted in DMEM containing 1% bovine serum albumin (BSA). Aliquots (10 μl) of each dilution were placed in the wells of the assay plates.

5.3. Human Foreskin Fibroblast (HFF) Mitogen Assay for PDGF

HFF stocks were stored frozen; freezing was at passage 13. Prior to use, HFF were thawed, and grown in T75 flasks until confluent, which usually occurred at 5–7 days. Growth medium contained Dulbecco's Modified Eagles Medium (DMEM), 20% fetal bovine serum (FBS), 1 mM sodium pyruvate, 300 μg/ml L-glutamine, 100 U/ml penicillin, and 100 μg/ml streptomycin. Cells were incubated at 37° C., in humidified 7% $CO_2$, 93% air atmosphere. At confluency, cells were passaged by rinsing the monolayer with phosphate buffered saline (PBS) lacking $Ca^{++}$ and $Mg^{++}$, dissociating them in trypsin containing EDTA, and diluting them with Growth Medium. Cells were passaged no more than 8 times after thawing.

To assay for PDGF, HFFs were plated as follows. The cells were rinsed and dissociated with trypsin as above. The trypsinized cells were pelleted, and resuspended to a concentration of $1 \times 10^5$ cells/ml in medium similar to Growth Medium, except that 5% FBS replaced 20% FBS; 100 μl of suspension was dispensed into each well of a 96 well microtiter plate, and the cells were incubated 5–6 days under the above described conditions.

PDGF in the sample was determined by monitoring $^3$H-thymidine incorporation into HFF DNA stimulated by PDGF. Samples were added to the wells containing HFF monolayers, and the assay plates incubated as above for 18 hours. The HFF cultures were then pulsed with [Methyl-$^3$H] thymidine (10 μC/ml final concentration. 1 μC/well) at 37° C., under the above described incubation conditions for 8 hours. After incubation, the cells were rinsed with PBS and fixed. Fixing was by incubation with 5% trichloracetic acid (TCA) and then 100% methanol for 15 minutes, followed by drying in air. The cells were then solubilized with 0.3N NaOH, and counted in a liquid scintillation counter.

Control samples were treated as the samples described above, and were prepared as follows. For positive controls. PDGF, purchased from PDGF, Inc., was dissolved to a final concentration of 100 ng/ml in DMEM containing 10 mg/ml BSA. A standard curve was prepared: the first point was 10 ng/ml, the remaining points were 2-fold serial dilutions. Each dilution was tested in triplicate. Negative controls, which lacked both sample and control PDGF, were also run.

Modifications of the above-described modes for carrying out the invention that are obvious to those of skill in the fields related to the invention are intended to be within the scope of the following claims.

What is claimed is:

1. A recombinant protein preparation comprising a PDGF A-chain homodimer comprised of two disulfide linked chains, each of said chains comprising the amino acid sequence numbered 87–211, inclusive, of FIG. 1, or an analog of said sequence that comprises less than 10 amino acid variations and retains PDGF biological activity as measured using a human foreskin fibroblast mitogen assay, wherein said protein preparation is produced in a nonhuman cell such that said protein preparation is free of other human proteins.

2. The protein preparation of claim 1, further comprising a pharmaceutically acceptable excipient.

3. The protein preparation of claim 2, wherein the pharmaceutically acceptable excipient is suitable for topical administration.

4. The recombinant protein preparation of claim 1, wherein the preparation comprises a PDGF A-chain homodimer comprised of two disulfide linked chains, each of said chains comprising the amino acid sequence numbed 87–211, inclusive, of FIG. 1.

5. The recombinant protein preparation of claim 1, wherein the analog comprises less than 10 amino acid substitutions.

6. The recombinant protein preparation of claim 5, wherein the analog comprises less than 3 amino acid substitutions.

7. A recombinant protein preparation comprising a PDGF A-chain homodimer comprised of two disulfide linked chains, each of said chains comprising the amino acid sequence numbered 87–193, inclusive, of FIG. 1, wherein said protein preparation is produced in a nonhuman cell such that said protein preparation is free of other human protein.

8. The protein preparation of claim 7, further comprising a pharmaceutically acceptable excipient.

9. The protein preparation of claim 8, wherein the pharmaceutically acceptable excipient is suitable for topical administration.

10. A recombinant protein preparation comprising a PDGF A-chain homodimer comprised of two disulfide linked chains, each of said chains comprising the amino acid sequence numbered 87–196, inclusive, of FIG. 1 of the amino acid sequence numbered 87–196, inclusive, of FIG. 2, wherein said protein preparation is produced in a nonhuman cell such that said protein preparation is free of other human protein.

11. The protein preparation of claim 10, further comprising a pharmaceutically acceptable excipient.

12. The protein preparation of claim 11, wherein the pharmaceutically acceptable excipient is suitable for topical administration.

* * * * *